(12) United States Patent
Geiger et al.

(10) Patent No.: US 12,201,563 B2
(45) Date of Patent: Jan. 21, 2025

(54) MODULAR INSERT FOR A PATIENT ROOM

(71) Applicant: EIR Healthcare Holdings, Inc., Philadelphia, PA (US)

(72) Inventors: Gunter Grant Geiger, Philadelphia, PA (US); Patrick Fenningham, Philadelphia, PA (US); Paul Coughlin, Brooklyn, NY (US); Samantha Fox, Philadelphia, PA (US); Greg Sloditskie, Walnut Creek, CA (US)

(73) Assignee: EIR Healthcare Holdings, Inc., Philadelphia, PA (US)

( * ) Notice: Subject to any disclaimer, the term of this patent is extended or adjusted under 35 U.S.C. 154(b) by 774 days.

(21) Appl. No.: 17/063,603

(22) Filed: Oct. 5, 2020

(65) Prior Publication Data

US 2021/0100708 A1    Apr. 8, 2021

Related U.S. Application Data

(60) Provisional application No. 62/910,253, filed on Oct. 3, 2019.

(51) Int. Cl.
*A61G 12/00* (2006.01)
*A61B 90/00* (2016.01)

(52) U.S. Cl.
CPC ............ *A61G 12/004* (2013.01); *A61B 90/00* (2016.02); *A61G 12/005* (2013.01)

(58) Field of Classification Search
CPC .... A61G 12/004; A61G 90/00; A61G 12/005; A61G 12/002; E04H 3/08; A61B 90/00
See application file for complete search history.

(56) References Cited

U.S. PATENT DOCUMENTS 3,267,955 A * 8/1966 Logan ...................... E04H 3/08
454/251
3,623,296 A    11/1971 Joseph
(Continued)

FOREIGN PATENT DOCUMENTS

| CA | 998216 A | 10/1976 |
|---|---|---|
| DE | 1958705 A | 6/1970 |

(Continued)

OTHER PUBLICATIONS

Al Xueming, "Public Building Design", Southeast University Press, Sep. 30, 2009, pp. 281-285.

(Continued)

*Primary Examiner* — Theodore V Adamos
(74) *Attorney, Agent, or Firm* — Kaplan Breyer Schwarz, LLP

(57) ABSTRACT

A modular insert for a patient room, the modular insert having a headwall with supply connections for electricity and medical grade vacuum, air and oxygen, and a lightbridge with medical examination lighting, the lightbridge coupled to the headwall. Further a lifting frame for transporting the modular insert to a patient room and facilitating installation thereof in the patient room, the lifting frame having a floor member for removably attaching to the headwall and a wall member for removably attaching to the lightbridge, the wall member pivotally attached to the floor member. Still further, a method for transporting the modular insert to a patient room and installing the modular insert in the patient room using the lifting frame.

21 Claims, 22 Drawing Sheets

(56) References Cited

U.S. PATENT DOCUMENTS

| | | | |
|---|---|---|---|
| 3,733,763 A | | 5/1973 | Drucker |
| 3,818,654 A | | 6/1974 | Schramm |
| 3,872,635 A | | 3/1975 | Miram |
| 4,448,434 A | * | 5/1984 | Anderson ............... B62B 1/12 280/654 |
| 4,475,322 A | * | 10/1984 | Russo ............... A61G 12/002 52/27 |
| 4,612,741 A | | 9/1986 | Jacobson |
| 4,650,437 A | | 3/1987 | Sitkus |
| 4,752,143 A | | 6/1988 | Lautenschlaeger, Jr. |
| 4,766,708 A | | 8/1988 | Sing |
| 4,959,933 A | | 10/1990 | Lappi |
| 5,038,254 A | * | 8/1991 | Fabbri ............... F21S 2/005 362/147 |
| 5,265,384 A | | 11/1993 | Menke et al. |
| 5,299,338 A | * | 4/1994 | Foster ............... A61G 12/004 248/282.1 |
| 5,452,807 A | * | 9/1995 | Foster ............... F16M 11/2014 211/168 |
| 5,528,866 A | | 6/1996 | Yulkowski |
| 5,656,491 A | | 8/1997 | Cassani et al. |
| 5,845,583 A | | 12/1998 | Jensen |
| 6,079,162 A | | 6/2000 | Hein |
| 6,145,253 A | | 11/2000 | Gallant et al. |
| 6,360,494 B1 | | 3/2002 | Emerson |
| 6,533,532 B1 | * | 3/2003 | Schmitt ............... B62B 5/0023 414/592 |
| 6,681,531 B2 | | 1/2004 | McManus |
| 6,748,704 B2 | | 6/2004 | Eguchi et al. |
| 6,758,318 B2 | | 7/2004 | Weaver |
| 7,127,999 B2 | | 10/2006 | Roane |
| 7,174,678 B2 | | 2/2007 | Gallant |
| 7,513,822 B2 | | 4/2009 | Flitsch |
| 7,549,893 B1 | | 6/2009 | Walker et al. |
| 7,770,860 B1 | * | 8/2010 | Culpepper ......... F16M 11/2014 248/324 |
| 8,522,488 B1 | | 9/2013 | Newkirk et al. |
| 8,640,391 B2 | | 2/2014 | Newkirk et al. |
| 8,919,849 B1 | * | 12/2014 | Robertson ........... E04B 1/34336 296/24.38 |
| 9,010,031 B1 | | 4/2015 | Webb et al. |
| 9,617,748 B2 | | 4/2017 | Wilson et al. |
| 10,167,645 B2 | | 1/2019 | Geiger |
| 10,883,287 B2 | | 1/2021 | Geiger |
| 2002/0023393 A1 | | 2/2002 | Mcmanus |
| 2002/0046518 A1 | | 4/2002 | Eguchi et al. |
| 2004/0199996 A1 | * | 10/2004 | Newkirk ............... F16M 11/26 5/81.1 R |
| 2005/0193643 A1 | | 9/2005 | Pettus |
| 2006/0143997 A1 | | 7/2006 | Libenson |
| 2007/0007418 A1 | * | 1/2007 | Lubbers ............ F16M 11/2014 248/326 |
| 2007/0067911 A1 | * | 3/2007 | Graham ............... A61G 12/004 5/658 |
| 2007/0144079 A1 | | 6/2007 | Hourihan |
| 2007/0199262 A1 | * | 8/2007 | Kern ............... A61B 5/02055 52/234 |
| 2007/0199263 A1 | | 8/2007 | Kern et al. |
| 2008/0287924 A1 | | 11/2008 | Mangiardi |
| 2012/0323090 A1 | * | 12/2012 | Bechtel ............... A61B 5/1113 600/595 |
| 2013/0232885 A1 | * | 9/2013 | Gallant ............... A61G 7/1042 52/29 |
| 2014/0318077 A1 | | 10/2014 | Case |
| 2016/0090730 A1 | | 3/2016 | Segall |

FOREIGN PATENT DOCUMENTS

| | | | | |
|---|---|---|---|---|
| DE | 3036468 A1 | | 5/1982 | |
| EP | 0118957 A2 | | 9/1984 | |
| EP | 0215212 A2 | * | 3/1987 | |
| EP | 0882851 A2 | * | 12/1998 | |
| EP | 3482733 A1 | * | 5/2019 | ............. A47C 17/52 |
| FR | 2614736 A1 | * | 11/1988 | |
| NL | 7404345 A | | 10/1975 | |
| WO | WO-9615337 A1 | * | 5/1996 | ............. A61B 50/10 |
| WO | WO-2005120294 A2 | * | 12/2005 | ............. A47C 17/52 |
| WO | 2006/071870 A2 | | 7/2006 | |
| WO | 2015/097226 A2 | | 7/2015 | |
| WO | WO-2017037612 A1 | * | 3/2017 | |

OTHER PUBLICATIONS

Applicant Initiated Interview Summary (PTOL-413) Mailed on Aug. 13, 2020 for U.S. Appl. No. 16/226,358.

Applicant Initiated Interview Summary (PTOL-413) Mailed on Feb. 2, 2018 for U.S. Appl. No. 15/106,653.

Authorized Officer: Agnes Wittmann-Regis, "English Translation of the International Preliminary Report On Patentability" issued in counterpart International Patent Application No. PCT/EP2014/079181, dated Jul. 7, 2016, Publisher: PCT.

English Translation of Office Action issued in Chinese Patent Application No. 201480074694.1 on Sep. 16, 2019.

"Chinese Office Action", Chinese Patent Application No. 201480074694. 1, Mar. 16, 2018, 25 pp.

"Office Action" issued in corresponding German Patent Application No. 102013114816.6 with translation, dated Aug. 5, 2014, Published in: DE.

"International Search Report and Written Opinion issued" in counterpart International Patent Application No. PCT/EP2014/079181, dated Jul. 27, 2015, Publisher: PCT, Published in: WO.

Final Office Action issued in counterpart Chinese patent application No. 201480074694.1, Apr. 9, 2020, 6 pp.

Final Office Action received for U.S. Appl. No. 16/226,358, mailed on Feb. 6, 2020.

Final Rejection Mailed on Oct. 5, 2017 for U.S. Appl. No. 15/106,653.

List of references Mailed on Apr. 24, 2017 for U.S. Appl. No. 15/106,653.

List of references Mailed on Aug. 15, 2018 for U.S. Appl. No. 15/106,653.

List of references Mailed on Mar. 16, 2018 for U.S. Appl. No. 15/106,653.

List of references Mailed on Oct. 5, 2017 for U.S. Appl. No. 15/106,653.

Non-Final Rejection Mailed on Apr. 24, 2017 for U.S. Appl. No. 15/106,653.

Non-Final Rejection Mailed on Mar. 16, 2018 for U.S. Appl. No. 15/106,653.

Non-Final Rejection received for U.S. Appl. No. 16/226,358, mailed on Jun. 26, 2019, 13 pages.

Notice of Allowance and Fees Due (PTOL-85) Mailed on Aug. 13, 2020 for U.S. Appl. No. 16/226,358.

Notice of Allowance received for U.S. Appl. No. 15/106,653, mailed on Aug. 15, 2018, 07 pages.

Office Action issued in related Indian Patent Application No. 201637021032 on Aug. 7, 2019.

Requirement for Restriction/Election Mailed on Feb. 3, 2017 for U.S. Appl. No. 15/106,653.

* cited by examiner

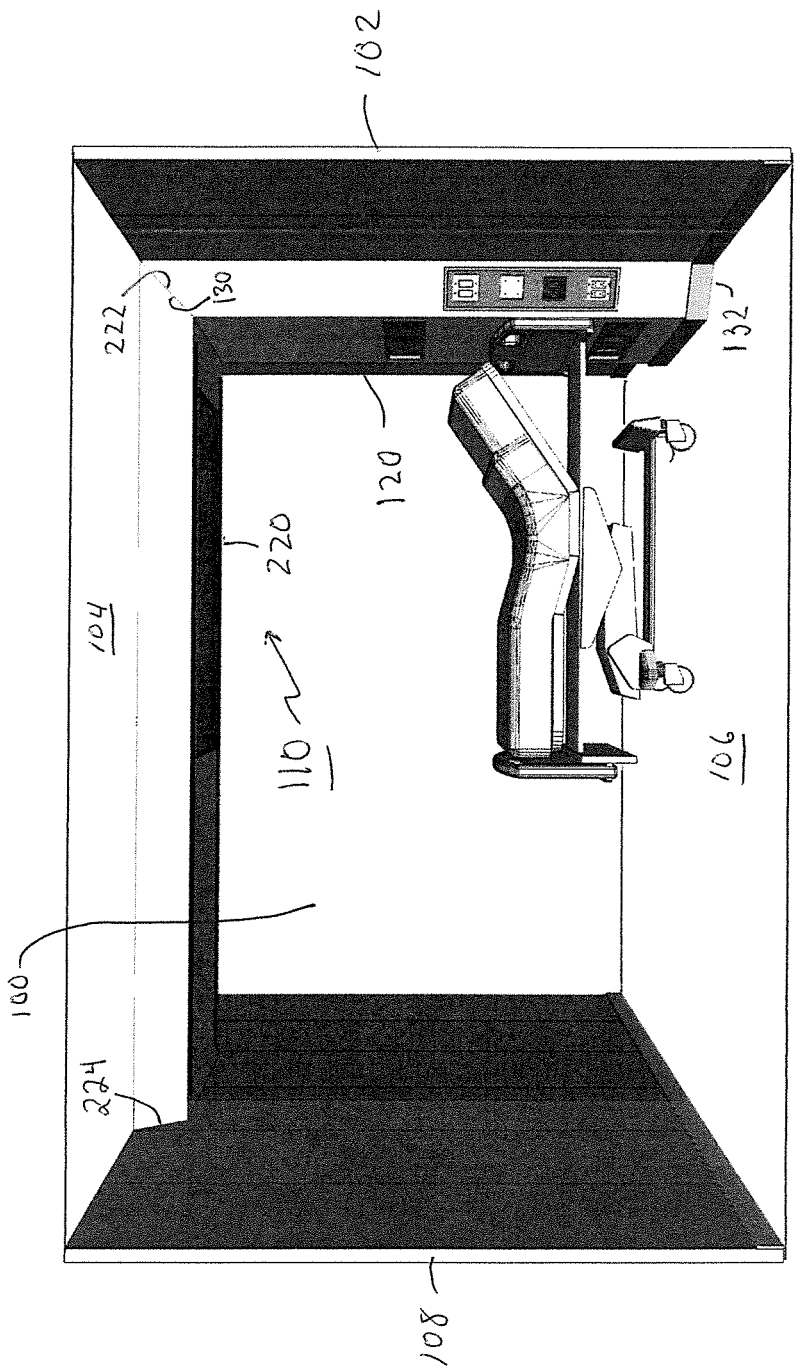

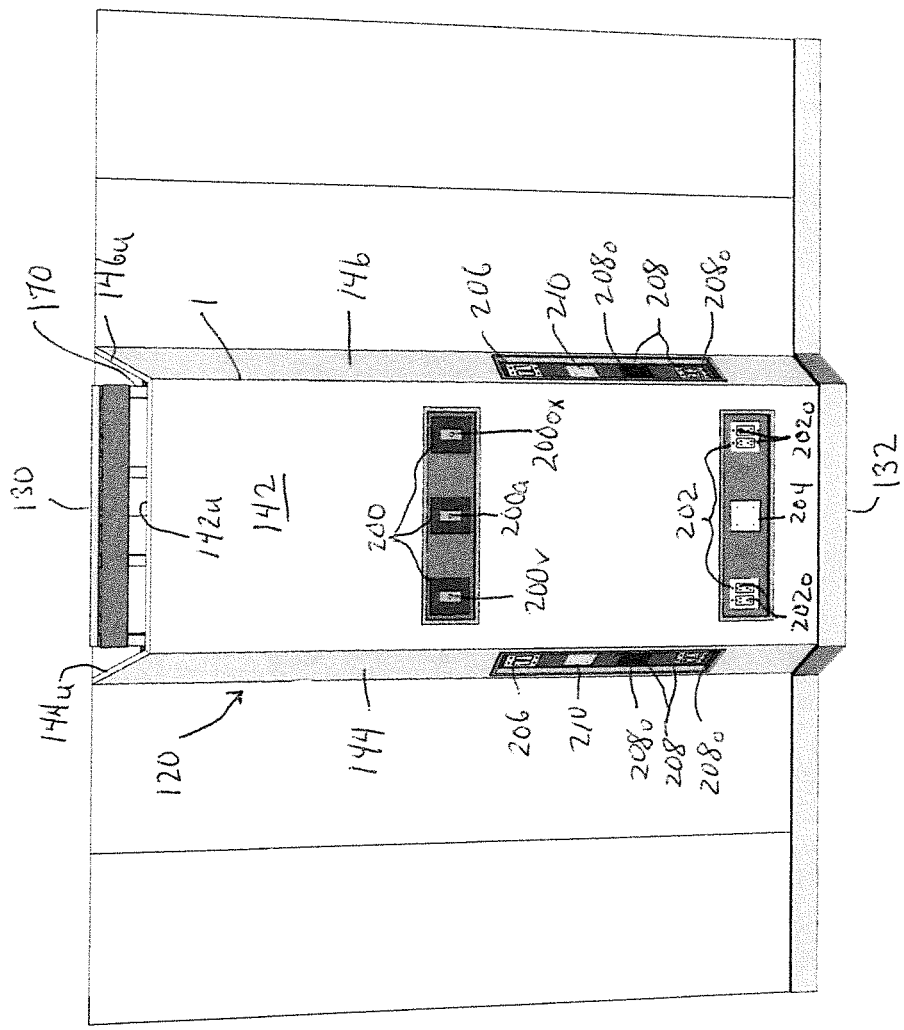

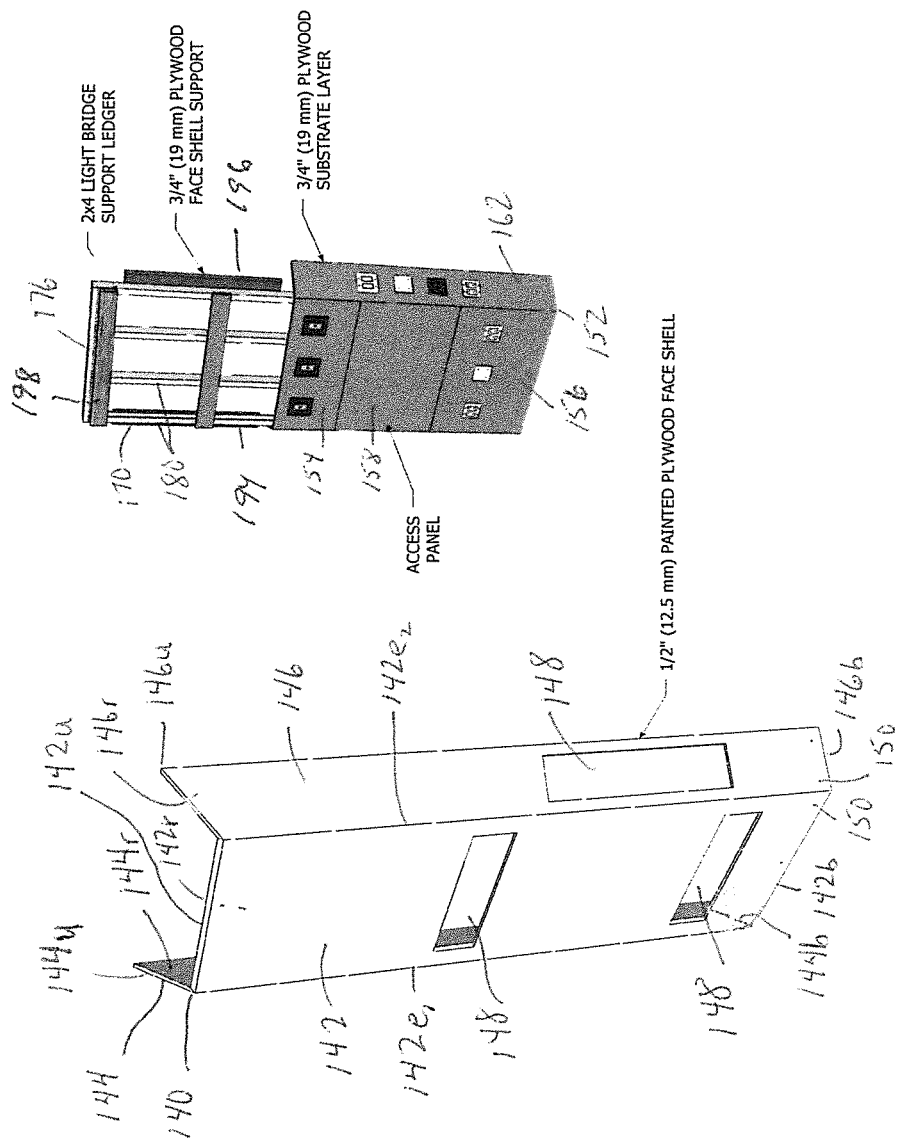

HEADWALL DETAIL 1

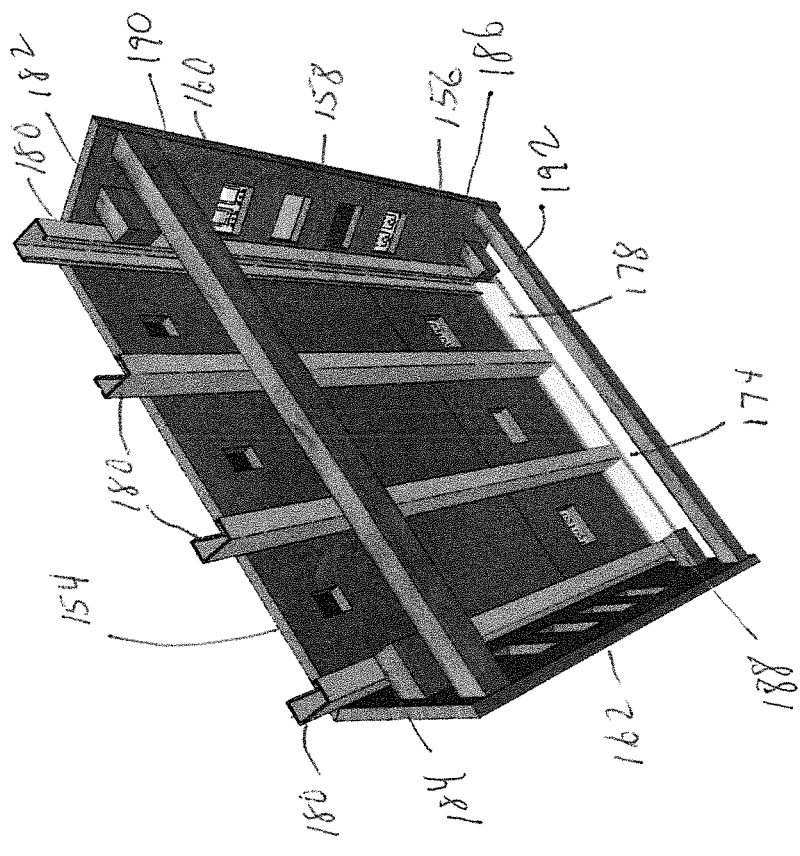

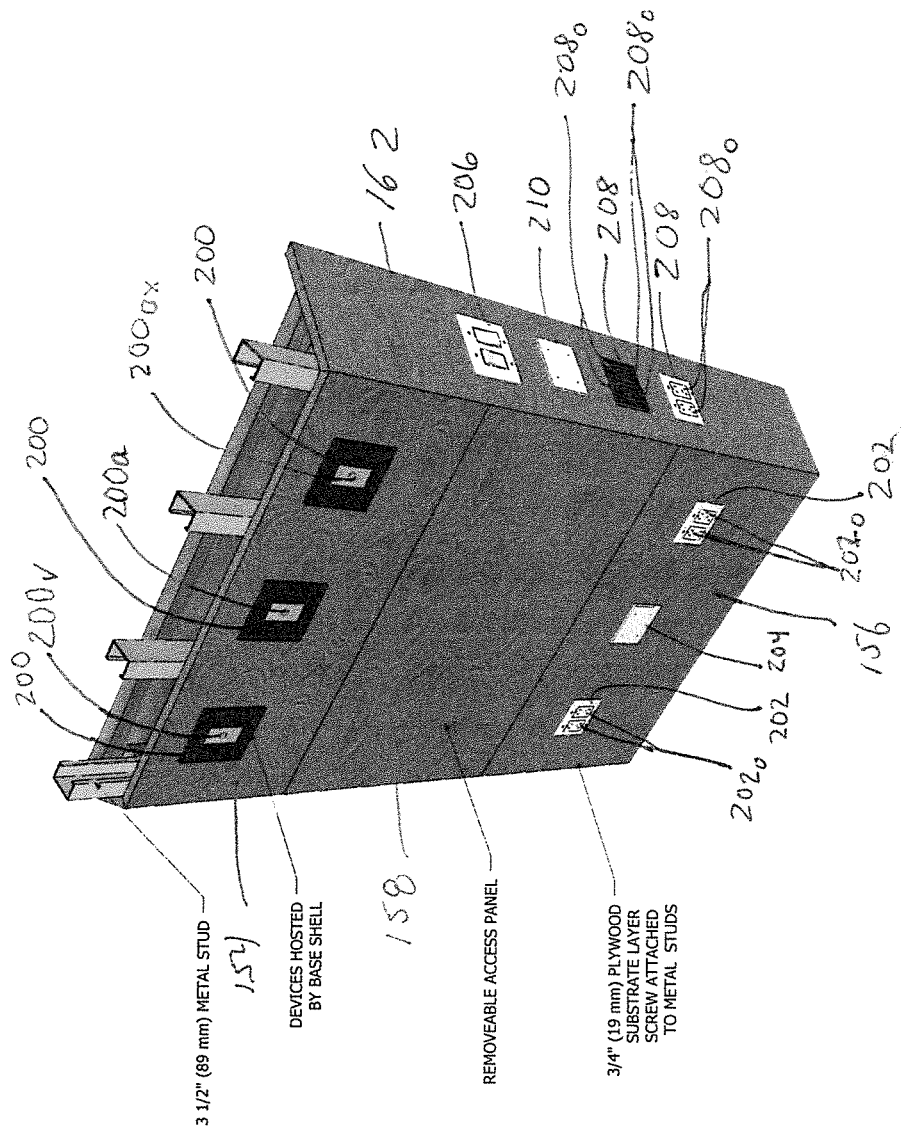

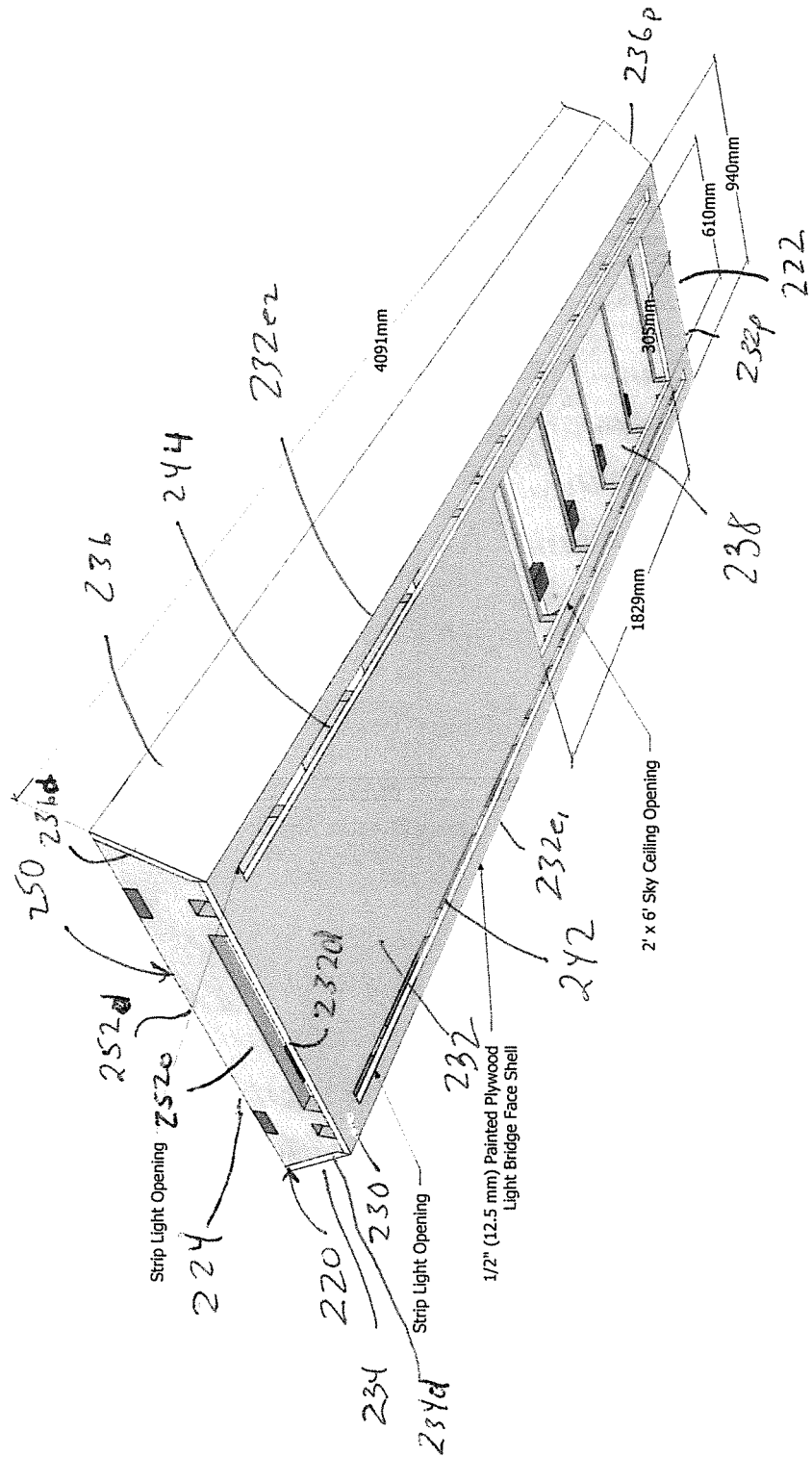

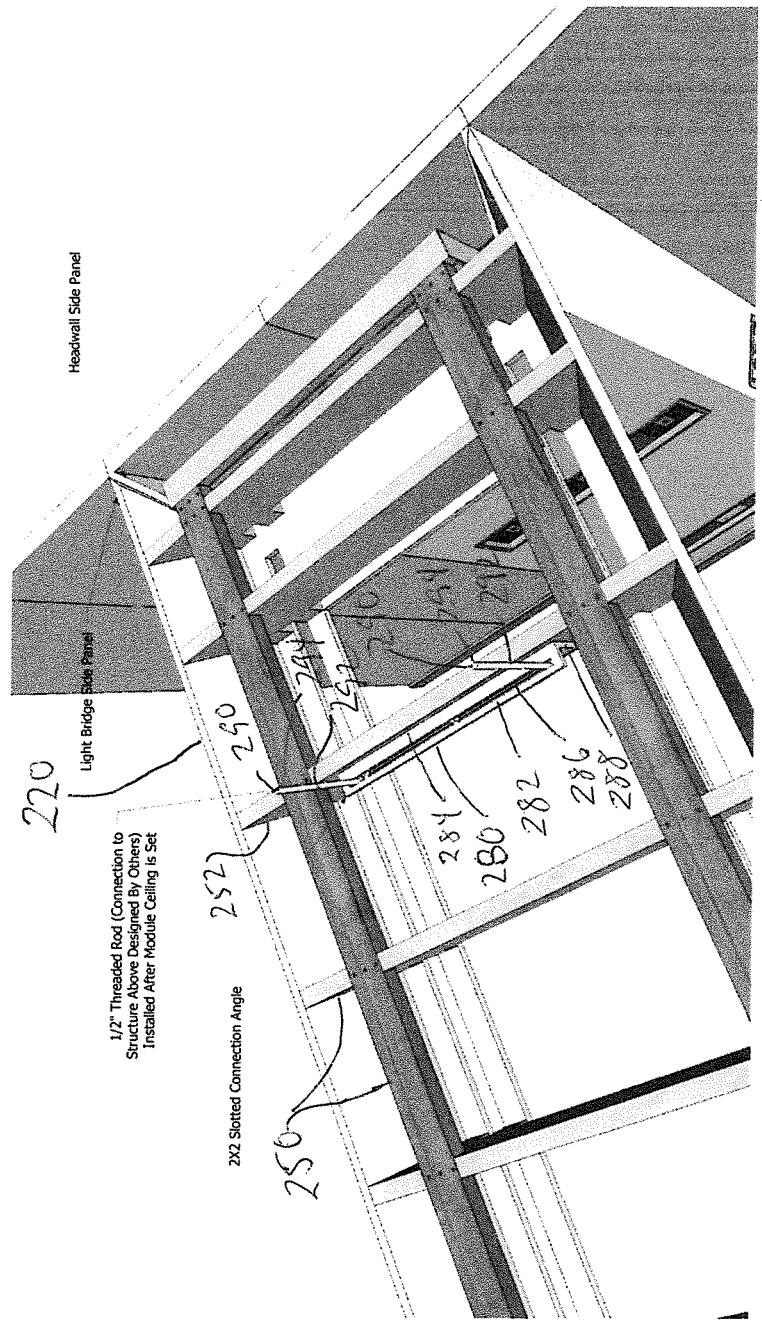

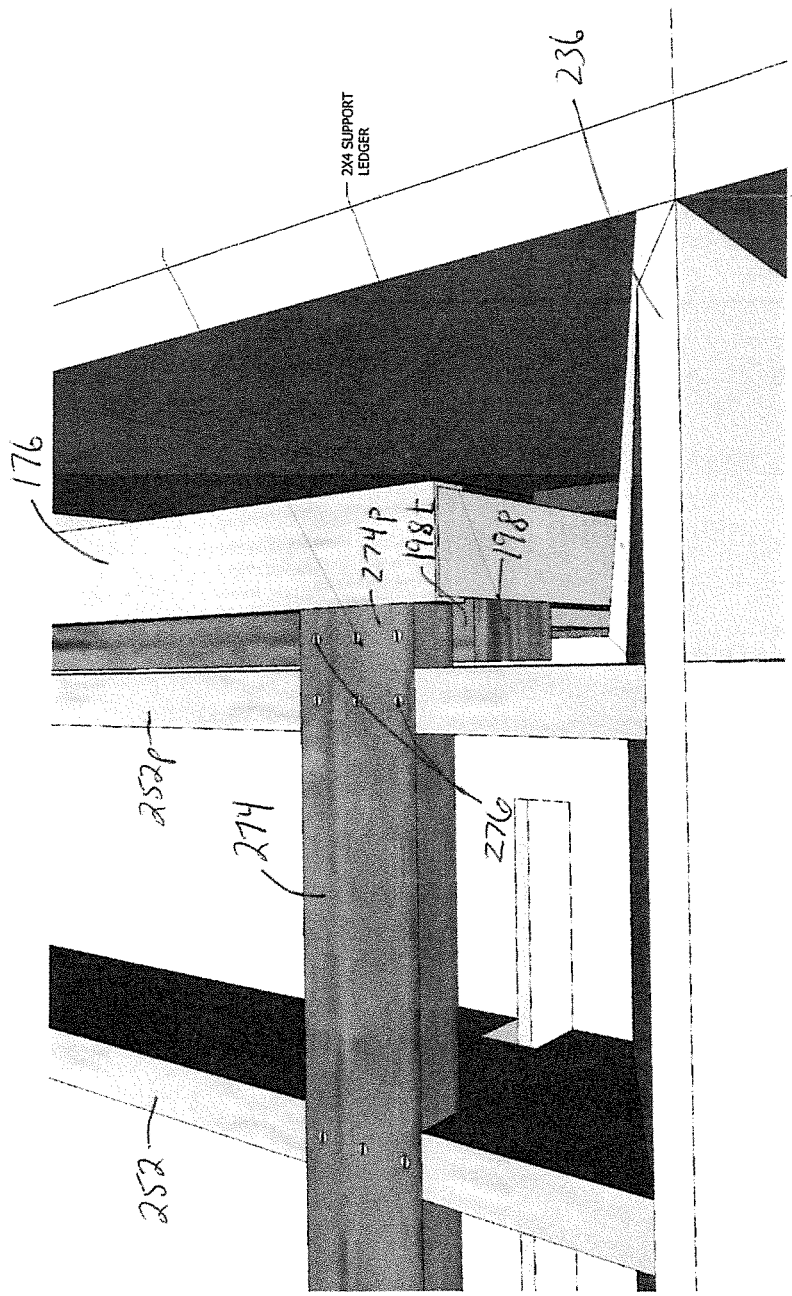

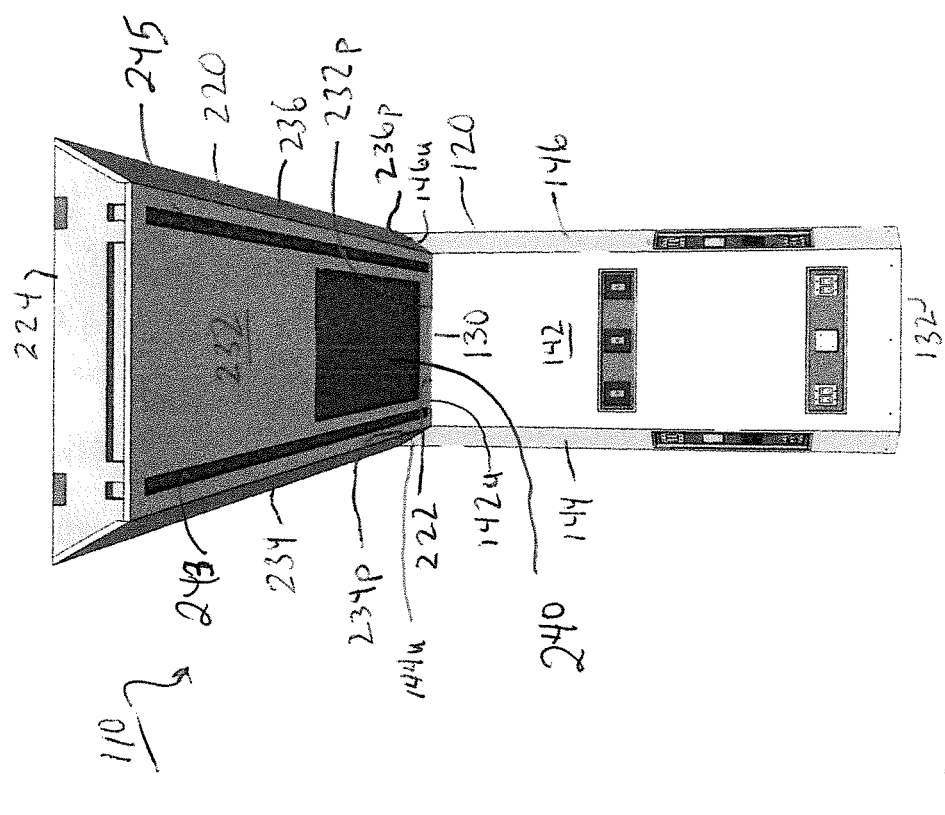

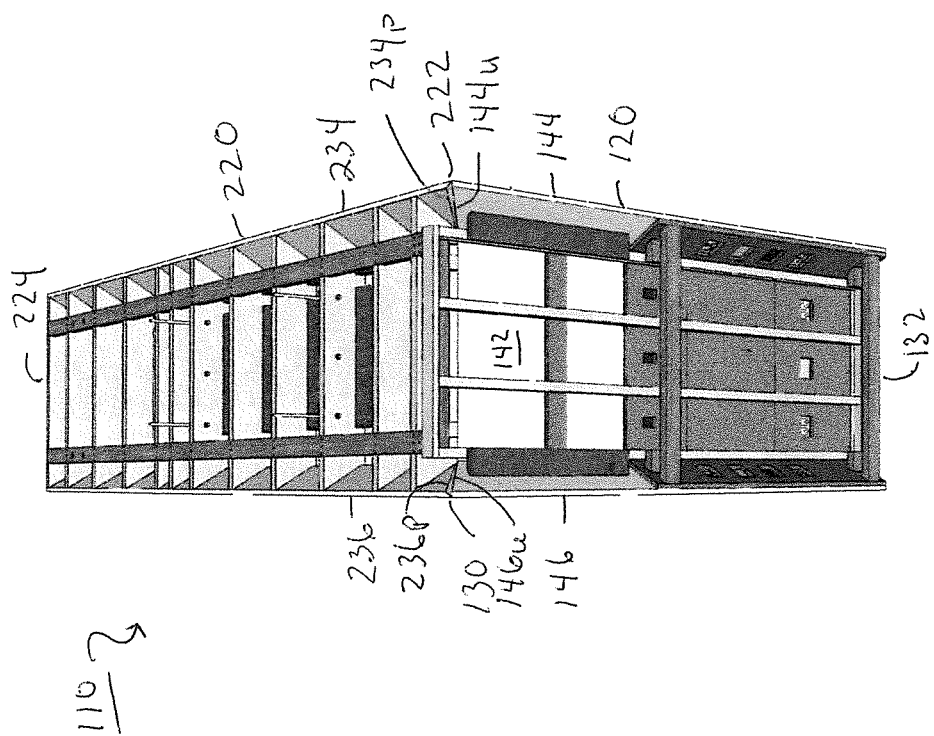

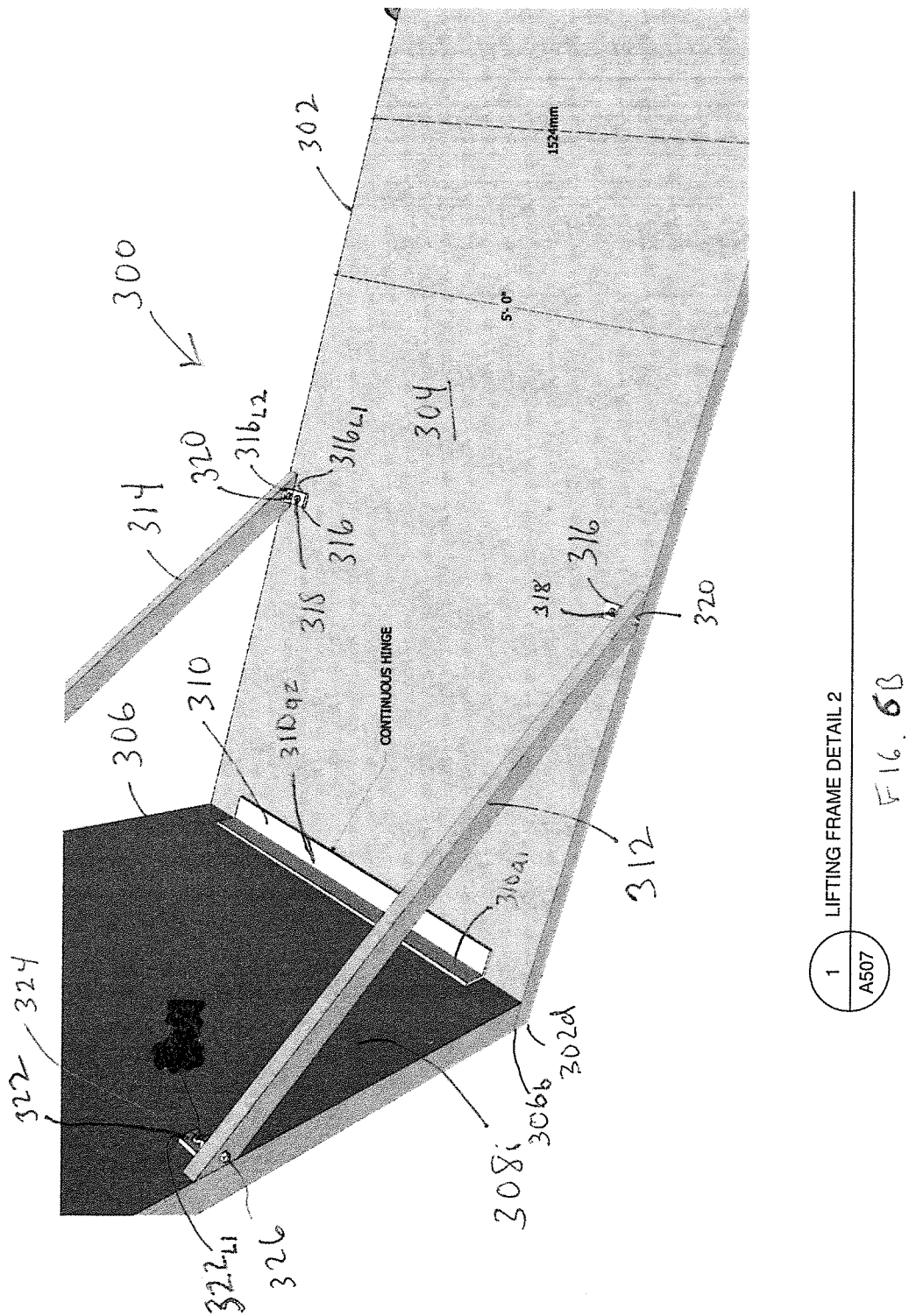

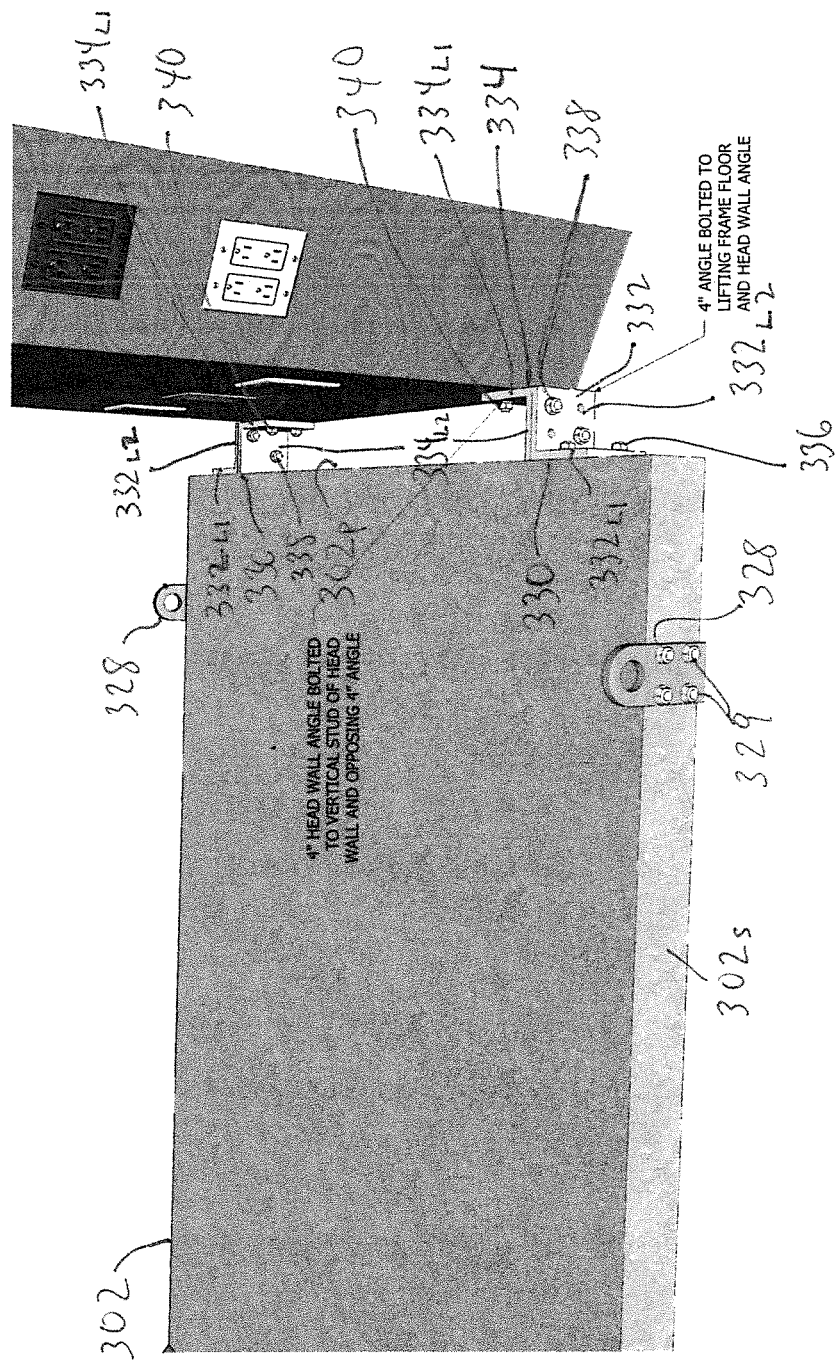

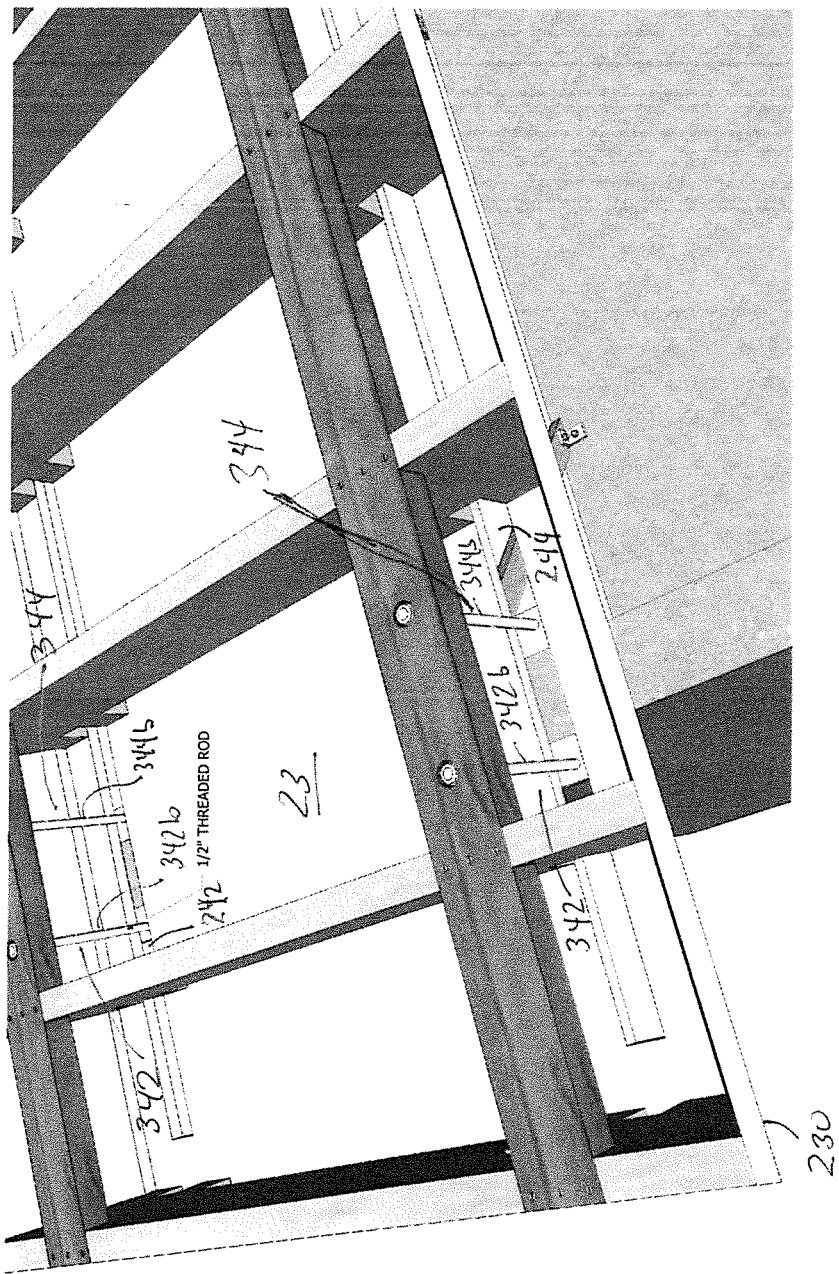

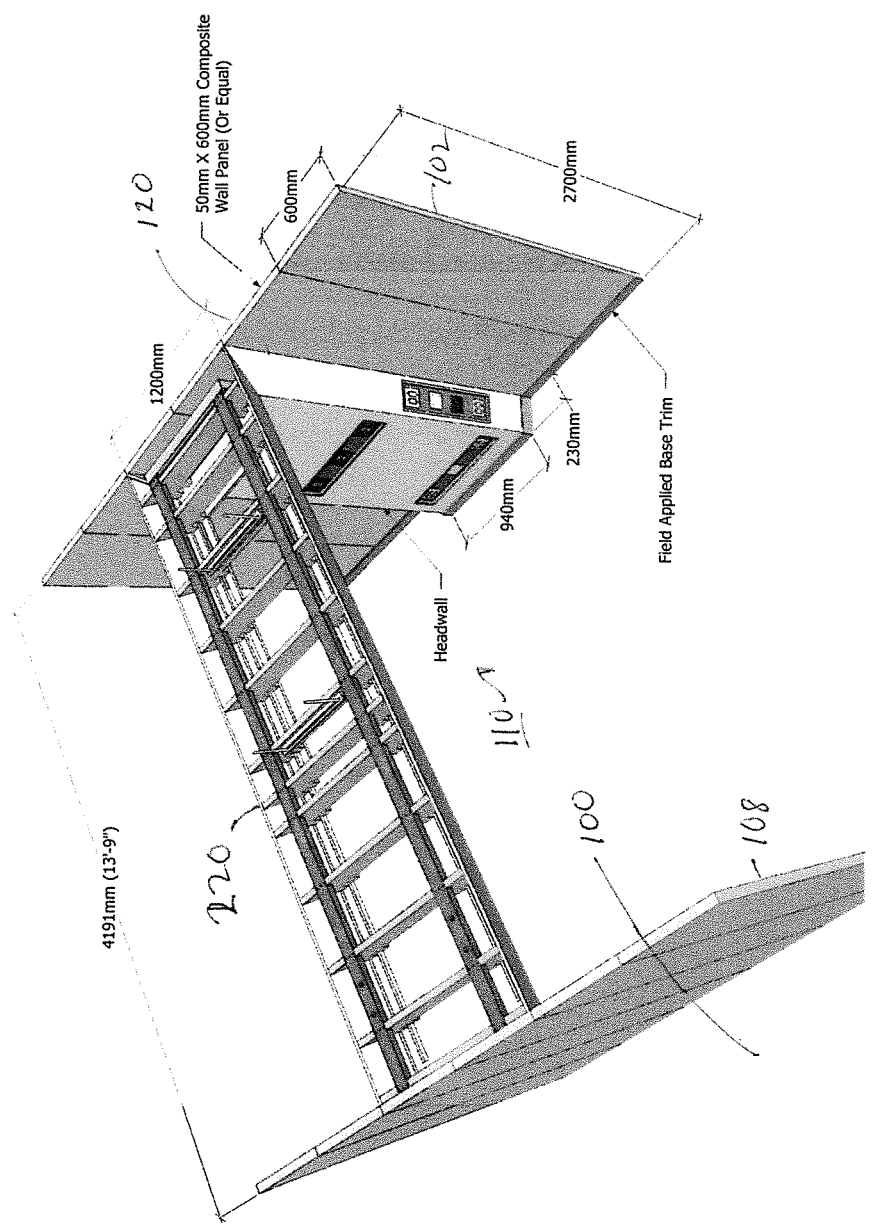

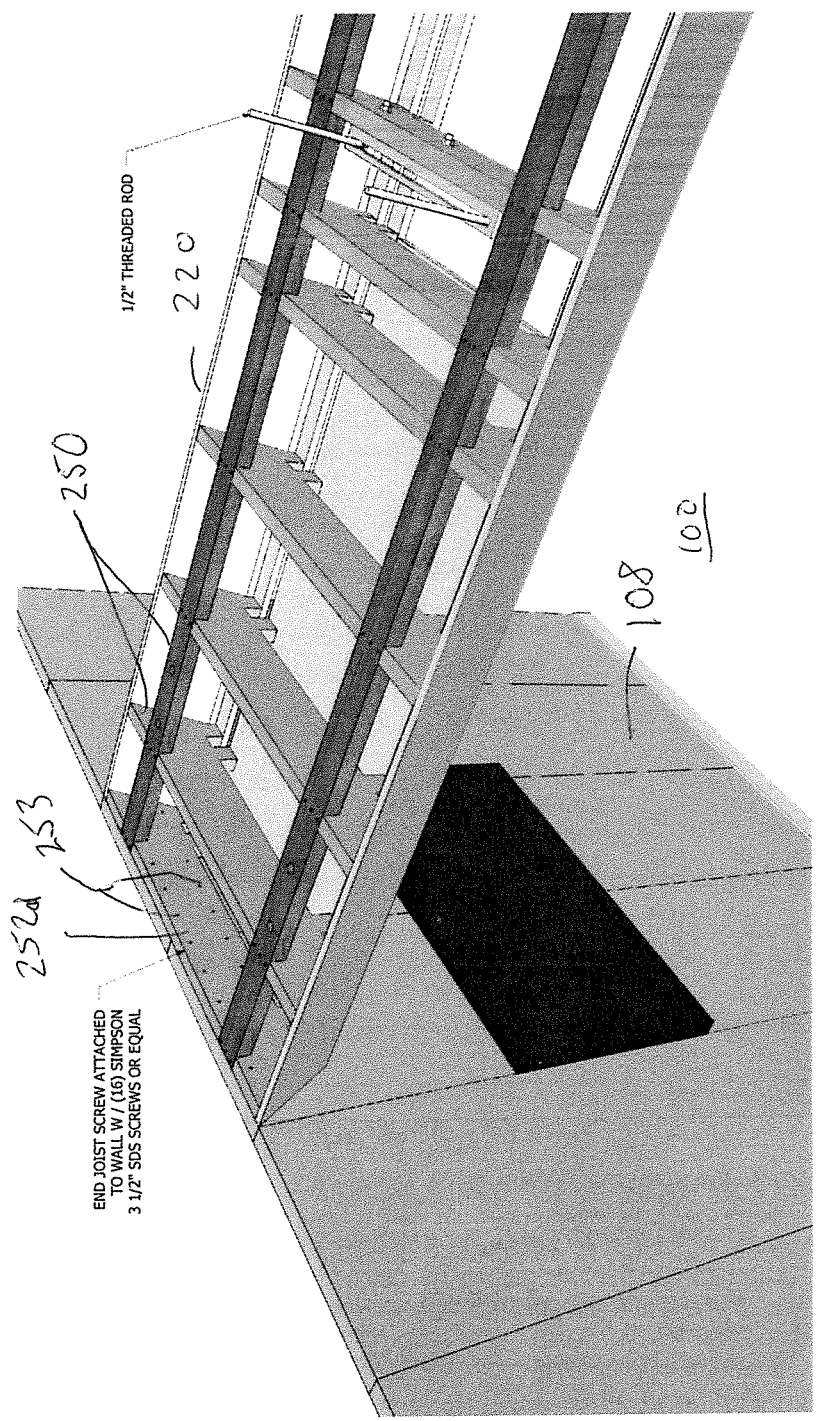

MODULAR INSERT FOR A PATIENT ROOM

RELATED APPLICATIONS

This application claims priority to U.S. Provisional Application Ser. No. 62/910,253, filed Oct. 3, 2019, whose entire disclosure is incorporated herein by reference.

FIELD

The present disclosure relates to modular medical care facilities. More particularly the present disclosure relates to a modular insert for providing medical gas and electric services for a patient room of a medical care facility, a lifting frame and method for transporting a modular insert to a patient room and installing the modular insert in the patient room, and a patient room having a modular insert.

BACKGROUND

Part of the construction costs of a medical care facility, such as a hospital, an ambulatory surgical center, an urgent care clinic, or any other medical care or like facility, depends on the cost of the medical equipment and the installation thereof during construction. One significantly costly item installed in most patient rooms of a medical care facility is the medical headwall and the medical examination lighting. Medical headwalls typically provide medical gas and electrical services adjacent the patient bed. Modular versions of such headwalls simplify and reduce the cost of the installation of these services, but do not include medical lighting.

Accordingly, there is a need for a modular insert that provides medical gas, electrical services, and medical exam lighting for a patient room in a medical care facility, which installs easily and is less expensive than conventionally constructed headwalls and medical examination lighting.

SUMMARY

Disclosed herein is a modular insert for a patient room. In some embodiments, the modular insert comprises a headwall with supply connections for electricity, vacuum, air and oxygen and a lightbridge with medical examination lighting, wherein the lightbridge is coupled to the headwall.

In some embodiments of the modular insert, the headwall and the lightbridge are coupled in an L-shaped configuration.

In some embodiments of the modular insert, the headwall comprises an inner panel arrangement, wherein the supply connections are provided by the inner panel arrangement.

In some embodiments of the modular insert, the headwall further comprises a removable faceshell disposed over the inner panel arrangement, wherein the faceshell includes at least one window for accessing the supply connections.

In some embodiments of the modular insert, the inner panel arrangement comprises a removable access panel.

In some embodiments of the modular insert, the headwall is adapted to be electrically connected to electrical power of the patient room and supplies the lightbridge with electricity for the medical examination lighting.

In some embodiments of the modular insert, the headwall comprises a control device for the medical examination lighting of the lightbridge.

In some embodiments of the modular insert, the inner panel arrangement of the headwall comprises a front wall.

In some embodiments of the modular insert, the supply connections are provided by the front wall.

In some embodiments of the modular insert, the inner panel arrangement of the headwall comprises at least one side wall.

In some embodiments of the modular insert, the supply connections are further provided on the at least one side wall.

In some embodiments of the modular insert, the modular insert further comprises a wall frame, wherein the inner panel arrangement and the faceshell of the headwall are attached to the wall frame.

In some embodiments of the modular insert, the lightbridge further comprises a faceshell and a support structure, wherein the faceshell of the lightbridge is attached to the support structure.

In some embodiments of the modular insert, the support structure includes at least one ceiling attaching assembly.

In some embodiments of the modular insert, the faceshell of the lightbridge includes the medical examination lighting.

In some embodiments of the modular insert, the faceshell of the lightbridge includes an illuminable sky ceiling panel.

Further disclosed herein is a patient room comprising the modular insert described above wherein the patient room includes a wall and a ceiling, and wherein the modular insert is attached to at least one of the wall and the ceiling of the patient room.

In some embodiments of the modular insert, the modular insert further comprises a lifting frame removably attached to the modular insert, wherein the lifting frame is for transporting the modular insert to a patient room and facilitating installation of the modular insert in the patient room.

In some embodiments of the modular insert, the lifting frame comprises a floor member removably attached to the headwall and a wall member removably attached to the lightbridge.

In some embodiments of the modular insert, the wall member is pivotally attached to the floor member.

In some embodiments of the modular insert, the lifting frame further comprises at least one brace extending between the floor and wall members, wherein the at least one brace holding the wall member in a fixed position relative to the floor member.

Further disclosed herein is a method for transporting the modular insert described above to a patient room and facilitating installation thereof in the patient room. In some embodiments, the method comprises attaching a floor member of a lifting frame to the headwall of the modular insert, attaching a wall member of the lifting frame to the lightbridge of the modular insert, transporting the modular insert with the lifting frame attached thereto to a patient room, installing the modular insert in the patient room, and detaching the wall and floor members of the lifting frame from the lightbridge and headwall respectively.

In some embodiments of the method, the installation of the modular insert in the patient room includes attaching the modular insert to at least one of a wall and a ceiling of the patient room.

In some embodiments of the method, the method further comprises attaching the faceshell of the headwall to the wall frame and inner panel arrangement after detaching the floor member from the headwall.

Also disclosed herein is a lifting frame for transporting a modular insert to a patient room and facilitating installation of the modular insert in the patient room. In some embodiments, the lifting frame comprises a floor member for removably attaching to the headwall and a wall member for removably attaching to the lightbridge, wherein the wall member is pivotally attached to the floor member.

In some embodiments of the lifting frame, the lifting frame further comprises at least one brace extending between the floor and wall members, the at least one brace holding the wall member in a fixed position relative to the floor member.

BRIEF DESCRIPTION OF THE DRAWING

The disclosure is best understood from the following detailed description when read in conjunction with the accompanying drawing. It is emphasized that, according to common practice, the various features of the drawing are not necessarily to scale. On the contrary, the dimensions of the various features may be arbitrarily expanded or reduced for clarity. Like numerals denote like features throughout the specification and the drawing.

FIG. 1 is a perspective side view of an exemplary embodiment of a modular insert installed in a patient room.

FIG. 2A is a perspective front view of an exemplary embodiment of a medical headwall of the modular insert.

FIG. 2B is a perspective front view of an exemplary embodiment of a faceshell of the headwall.

FIG. 2C is a perspective front view of an exemplary embodiment of an inner panel arrangement of the headwall attached to an exemplary embodiment of a wall frame of the headwall.

FIG. 2E is an enlarged perspective rear view of the inner panel arrangement and wall frame with the wall frame shown in cross-section with a top section thereof removed for clarity.

FIG. 2F is an enlarged perspective front view of the inner panel arrangement and wall frame with the wall frame shown in cross-section with the top section thereof removed for clarity.

FIG. 3A is a perspective front view of an exemplary embodiment of a medical lightbridge of the modular insert.

FIG. 3E is a perspective top view of the proximal end of the lightbridge.

FIG. 4 is an enlarged perspective top view of the proximal end of the lightbridge and the top end of the headwall.

FIG. 5A is a perspective front view of an exemplary embodiment of the modular insert.

FIG. 5C is a perspective rear view of the modular insert of FIG. 5A.

FIG. 6B is a perspective side view of a portion of the lifting frame of FIG. 6A.

FIG. 6C is a perspective side view of a proximal end of a floor member of the lifting frame connected to a bottom end of the headwall of the modular insert.

FIG. 6E is a perspective top view showing the top end of the wall member of the lifting frame connected to the marginal distal end of the lightbridge of the modular insert.

FIG. 7A is a perspective top view of the modular insert installed in the patient room.

FIG. 7B is a perspective top view showing the distal end of the lightbridge connected to a wall of the patient room.

DETAILED DESCRIPTION

Figure 2D:
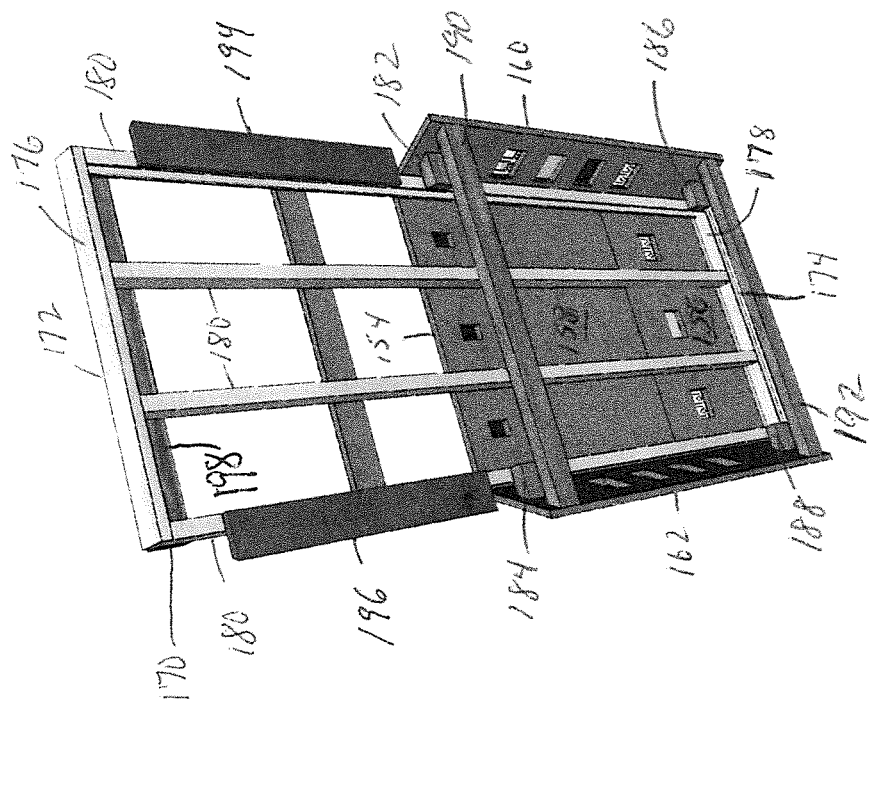
FIG. 2D is a perspective rear view of the inner panel arrangement and wall frame shown in FIG. 2C.

It should be understood that the phraseology and terminology used below for the purpose of description and should not be regarded as limiting. The use herein of the terms "comprising," "including," "having," "containing," and variations thereof are meant to encompass the structures and features recited thereafter and equivalents thereof as well as additional structures and features. Unless specified or limited otherwise, the terms "attached," "mounted," "affixed," "connected," "supported," "coupled," and variations thereof are used broadly and encompass both direct and indirect forms of the same.

Referring now to the drawings and initially to FIG. 1, there is shown a modular insert 110 for a patient room 100 of a medical care facility according to an exemplary embodiment of the present disclosure. The medical care facility can be a hospital, an ambulatory surgical center, an urgent care clinic, a nursing home, a doctor's office, or any other medical care or like facility where a patient can obtain medical care. In some embodiments, the patient room can be a modular patient room of a modular medical care facility. The modular insert 110 includes a medical headwall 120 and a medical lightbridge 220. The headwall 120 provides various electrical and medical gas functions, and patient care accessories, and the lightbridge 220 provides medical examination lighting. The headwall 120 has a top end 130 and a bottom end 132, and the lightbridge 220 has a proximal end 222 and a distal end 224. The proximal end 222 of the lightbridge 220 is attached to the top end 130 of the headwall 120 so that the lightbridge 220 is positioned at a right angle with respect to the headwall 120, thereby forming an L-shaped configuration, as shown in FIG. 1. When the modular insert 110 is installed on a first wall 102 of the patient room 100, the top end 130 of the headwall 120 is located at or adjacent to a ceiling 104 of the patient room 100, the bottom end 132 of the headwall 120 is located at or adjacent to a floor 106 of the patient room 100, and the lightbridge 220 extends along the ceiling of the patient room 100 between the first wall 102 and an opposite second wall 108 of the patient room 100.

Referring to FIGS. 2A-2C, the headwall 120 includes an outer headwall faceshell 140 and an inner wall panel arrangement 152. The inner wall panel arrangement 152 is supported by a wall frame 170 and the outer headwall faceshell 140 is supported by the inner wall panel arrangement 152 and the wall frame 170.

As shown in FIGS. 2C-2E, the wall frame 170 includes a top track 176 that extends horizontally at the top end 172 thereof, a bottom track 178 that extends horizontally at a bottom end 174 thereof, and two or more spaced apart wall studs 180 that extend vertically from the top track 176 to the bottom track 178. The wall studs 180 are attached to the top and bottom tracks 176, 178 by metal screw or like fasteners. The top and bottom tracks 176, 178 allow the headwall 120 to be attached to the floor 106 and ceiling 104 of the patient room 100 using metal screw or like fasteners (not shown). The top and bottom tracks 176, 178 can comprise conventional U-shaped metal tracks made of steel or galvanized steel. The wall studs 180 can comprise conventional U-shaped metal studs made of steel or galvanized steel.

Referring still to FIGS. 2C-2E, the inner wall panel arrangement 152 provides continuous support for the outer headwall faceshell 140 to minimize damage potential to the faceshell 140 and hosts various medical gas outlet and electrical outlets boxes as will be described further on. The inner wall panel arrangement 152 includes an upper front panel 154, a lower front panel 156, a front access panel 158 between the upper and lower front panels 154, 156, a first side panel 160, and a second side panel 162. The panels 154, 156, 158, 160, 162 of the inner wall panel arrangement 152 can each comprise a sheet of plywood. The plywood sheets can have a thickness of 19 mm (¾ inches). The upper front panel 154 and the front access panel 158 can each be attached directly to the front sides of two or more of the wall studs 180 of the wall frame 170 with metal screw or like fasteners (not shown). The lower front panel 156 can be attached to the front sides of two or more of the wall studs 180 and the front side of the bottom track with metal screw or like fasteners (not shown).

Referring to FIGS. 2D and 2E, first and second upper side panel connectors 182, 184 and first and second lower side panel connectors 186, 188 are provided for attaching the first and second side panels 160, 162 of the inner wall panel arrangement 152 to the rear sides of the two outer-most wall studs 180 of the wall frame 170. The connectors 182, 184, 186, 188 can comprise conventional 2 inch thick by 4 inch wide blocks of wood. The connectors 182, 184, 186, 188 are attached to the back sides of their respective side panels 160, 162 and the back sides of their respective wall studs 180 with metal screw or like fasteners (not shown).

Referring still to FIGS. 2D and 2E, upper and lower horizonally extending braces 190 and 192 are provided for bracing the first and second side panels 160, 162 of the inner wall panel arrangement 152 to improve the structural rigidity of the headwall 120. The upper brace 190 has a first end that is attached to the back side of the first side panel 160 adjacent to an upper rear corner thereof and an opposite second end that is attached to the back side of the second side panel 162 adjacent to an upper rear corner thereof. Similarly, the lower rear brace 192 has a first end that is attached to the back side of the first side panel 160 adjacent to a lower rear corner thereof and an opposite second end that is attached to the back side of the second side panel 162 adjacent to a lower rear corner thereof.

As shown in FIGS. 2D and 2E, the length of the upper and lower braces 190, 192 is selected to position each of the side panels 160, 162 at an obtuse angle, relative to the front panels 154, 156, 158, as measured between the rear surface of the side panel 160, 162 and the rear surfaces of the front panels 154, 156, 158. In other embodiments, length the upper and lower braces can selected to position each of the side panels 160, 162 at a right angle or an acute angle relative to the front panels 154, 156, 158, as measured between the rear surface of the side panel 160, 162 and the rear surfaces of the front panels 154, 156, 158. The upper and lower braces 190, 192 can each comprise conventional 2 inch thick by 4 inch wide wood stud. In other embodiments, the upper and lower braces 190, 192 can comprise metal studs. The ends of the upper and lower braces 190, 192 are attached to the back sides of the side panels 160, 162 with metal screws or like fasteners (not shown).

Referring now to FIGS. 2A and 2F, the headwall 120 provides various electrical and medical gas functions, and patient care accessories, as mentioned earlier. More specifically, the upper front panel 154 of the inner wall panel arrangement 152 can include gas outlet boxes 200 which provide gas connections $200v$, $200a$, $200ox$ for various types of medical grade gas feeds including, without limitation, vacuum ($200v$), compressed air ($200a$), and oxygen ($200ox$). The lower front panel 156 can include one or more electrical boxes 202 that provide one or more electrical outlets $202o$ for connecting to electricity feeds. In some embodiments, the electrical outlets $202o$ can comprise one or more quad receptacles that each provide a hospital grade electrical circuit, e.g., 15-20 amps and 120-277 volts, and/or emergency critical power at a higher voltage, e.g., 700 volts. The lower front panel 156 can also include one or more blank wall plates 204 for future devices, electrical outlets, gas connections, and connections for other services, such as, but not limited to telephone, video, computer, and data services. One or both of the first and second side panels 160, 162 can include one or more button keypads 206 for controlling medical examination lights and a sky ceiling light provided in the lightbridge 220 (FIG. 5A), one or more electrical boxes 208 that provide one or more electrical outlets $208o$ (e.g. a quad receptacle with a hospital grade electrical circuit, e.g—15-20 amps and 120-277 volts, and a quad receptacle that provides emergency critical power at a higher voltage, e.g., 700 volts, and one or more blank wall plates 210 for future devices, electrical outlets, gas connections, and connections for other services, as mentioned above. The upper front panel 154, the lower front panel 156 and the side panels 160, 162 allow additional electrical outlets, gas connections, and devices to be added to the headwall 120 and allow existing electrical outlets, gas connections and devices to be removed and/or relocated. The front access panel 158 allows devices to be connected to their electrical and medical gas feeds and provides access for attaching the top and bottom tracks 176, 178 of the wall frame 170 to ceiling 104 and floor 106 of the patient room 100 with metal screw or like fasteners (not shown).

Referring now to FIGS. 2C and 2D, the wall frame 170 of the headwall 120 further includes vertically extending first and second headwall faceshell supports 194, 196. The faceshell supports 194, 196 are each attached to the back side of the first one of the wall studs 180 on each side of the wall frame 170 above the front panel 154 of the inner wall panel arrangement 152 with metal screw or like fasterners (not shown) The first and second faceshell supports 194, 196 can each comprise a sheet of plywood. The plywood sheets can have a thickness of 19 mm (¾ inches).

Referring still to FIGS. 2C and 2D, a horizontally extending lightbridge support ledger 198 is attached to the front sides of one or more of the wall studs 180 of the wall frame 170 just below the top track 176 with metal screw or like fasteners (not shown). The lightbridge support ledger 198 can comprise a conventional 2 inch thick by 4 inch wide wood stud.

Referring to FIG. 2B, the outer headwall faceshell 140 includes a front shell panel 142 and first and second side shell panels 144, 146. The first side shell panel 144 extends rearward from a first side edge $142e1$ of the front shell panel 142 and the second side shell panel 146 extends rearward from a second side edge $142e2$ of the front shell panel 142. The outer headwall faceshell 140 is configured to fit flush against the front surfaces of the front panels and side panels 154, 156, 158, 160, 162 of the inner wall panel arrangement 152, therefore, each side shell panel 144, 146 is positioned relative to the front shell panel 142 at the same angle (obtuse, right, or acute angle), measured between the rear surface of the side shell panel 144, 146 and the rear surface of the front shell panel 142, as the side panels 160, 162 of the inner wall panel arrangement 152 are angled relative to the front panels 154, 156, 158 of the inner wall panel arrangement 152, described earlier. The front and side shell panels 144, 146 of the outer headwall faceshell 140 each include windows 148 which align with and allow access to the medical gas outlet connections 200v, 200a, 200ox in the upper front panel 154, the electrical outlets 202o and blank wall plate 204 in the lower front panel 156 and the button keypads 206 electrical outlets 208o and blank wall plate 210 in the side panels 160, 162. The front and side shell panels 142, 144, 146 of the outer headwall faceshell 140 can be made of painted 12.5 mm (0.5 inch) thick sheets of plywood. In some embodiments, the plywood sheets forming the front shell panel 142 and side shell panels 144, 146 of the headwall faceshell 140 can be covered with an antimicrobial PVC wrap or film. In other embodiments, the front shell panel 142 and side shell panels 1444, 146 of the headwall faceshell 140 can be made of sheet metal covered with an antimicrobial PVC wrap or film.

The bottom or marginal bottom ends of the front and side shell panels 142, 144, 146 are attached to the bottom or marginal bottom ends of the lower front and side panels 156, 160, 162 of the inner wall panel arrangement 152 with metal screw or like fasteners and the upper or marginal upper ends of the side shell panels 144, 145 are each attached to a respective one of the first and second faceshell supports 194, 196 with metal screw or like fasteners.

If an end user wishes to change device types or locations at a future date, the end user can detach the outer headwall faceshell 140 from the inner wall panel arrangement 152 and faceshell supports 194, 196 and then detach and remove one or more of the upper front, lower front, and side wall panels 154, 156, 160, 162 of the inner wall panel arrangement 152 from the wall frame 170. Once the upper front, lower front, and/or side panel(s) 154, 156, 160, 162 is/are removed, the panel(s) 154, 156, 160, 162 can be modified to receive new devices or to relocate existing devices. Once modified, the upper front, lower front, and/or side panel(s) 154, 156, 160, 162 of the inner wall panel arrangement 152 can be re-attached to the wall frame 170. If necessary, new upper front, lower front, and/or side panel(s) can be attached to the wall frame 170. After the upper front, lower front, and/or side panels 154, 156, 160, 162 of the inner wall panel arrangement 152 have been re-attached to the wall frame 170, the outer headwall faceshell 140 can be re-attached to the inner wall panel arrangement 152 and faceshell supports 194, 196.

Figure 3B:
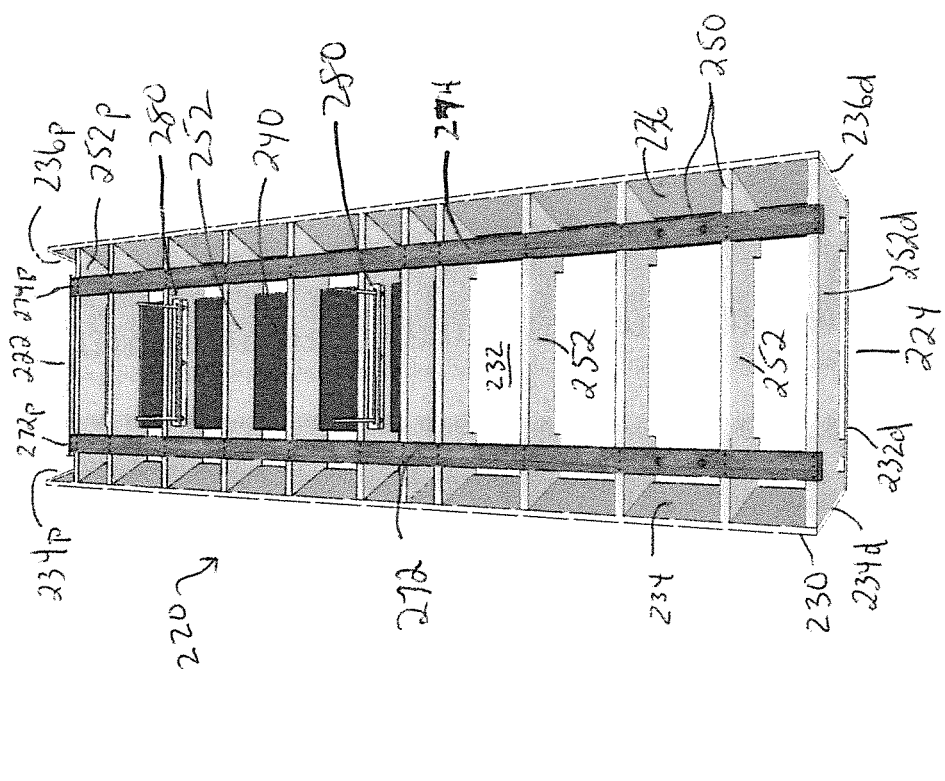
FIG. 3B is a perspective top view of the lightbridge of FIG. 3A from a distal end thereof.

Referring now to FIGS. 3A and 3B, the lightbridge 220 includes a lightbridge faceshell 230 and a support structure 250 on which the lightbridge faceshell 230 is mounted. The lightbridge faceshell 230 includes a front shell panel 232, a first side shell panel 234 and a second side shell panel 236. The first side shell panel 234 extends rearward from a first side edge of the front shell panel 232 and the second side shell panel 236 extends rearward from a second side edge of the front shell panel 232. The proximal ends 234p, 236p of the lightbridge side shell panels 234, 236 are configured to align with the upper ends 144u, 146u of the headwall side shell panels 144, 146 (FIG. 2B), therefore, each side shell panel 234, 236 of the lightbridge faceshell 230 is positioned, relative to the front shell panel 232 of the lightbridge faceshell 230, at the same angle (obtuse, right, or acute angle), measured between the rear surface of each lightbridge side shell panel 234, 236 and the rear surface of the lightbridge front shell panel 232, as the faceshell panels 144, 146 of the outer headwall faceshell 140 are angled relative to the headwall faceshell front panel 142, described earlier.

The front shell panel 232 of the lightbridge faceshell 230 includes an opening 238 at a marginal proximal end thereof, for receiving a translucent sky ceiling panel 240 and one or more lights (not shown) disposed behind the panel 240 that are adapted to statically and/or dynamically illuminate the sky ceiling panel 240. When illuminated, the sky ceiling panel 240 presents a static and/or dynamic image that facilitates patient recovery by reducing patient anxiety. The front shell panel 232 of the lightbridge faceshell 230 further includes at least one elongated opening 242, 244 located adjacent to each side edge of the front shell panel 232, which extends along the front shell panel 232 from a marginal proximal end to a marginal distal end thereof. Each enlongated opening 242, 244 receives a medical examination strip light 243, 245. The one or more sky ceiling lights (not shown) and the medical examination strip lights 243, 245 are electrically coupled to one or more of the earlier mentioned button keypads of the headwall 120, via a wire harness (not shown) that extends through the wall frame 170 of the headwall 120 and the support structure 250 of the lightbridge 220. Therefore, the one or more sky ceiling lights and the medical examination strip lights 243, 245 can each be controlled by one of the buttons of a corresponding one of the key pads 206 of the headwall 120. The front shell panel 232 and side shell panels 234, 236 of the lightbridge faceshell 230 can be made of painted 12.5 mm (0.5 inch) thick sheets of plywood. In some embodiments, the plywood sheets forming the front shell panel 232 and side shell panels 234, 236 of the lightbridge faceshell 230 can be covered with an antimicrobial PVC wrap or film. In other embodiments, the front shell panel 232 and side shell panels 234, 236 of the lightbridge faceshell 230 can be made of sheet metal covered with an antimicrobial PVC wrap or film.

Figure 3C:
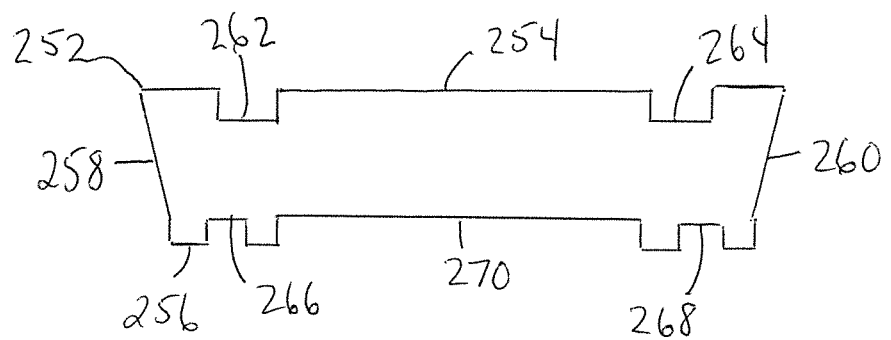
FIG. 3C is an elevational front or rear view of an exemplary embodiment of a joist of a support structure of the lightbridge.

As shown in FIG. 3B, the support structure 250 includes a plurality of spaced apart joists 252 which extend transversely between the side shell panels 234, 236 of the lightbridge faceshell 230 and first and second ceiling attachment struts 272, 274. As shown in FIG. 3C, each of the joists 252 is generally trapezoidal in shape and includes a top edge 254, a bottom edge 256, and first side edge 258 and a second side edge 260. The top edge 254 includes a first attachment strut notch 262 adjacent the first side edge 258 and a second attachment strut notch 264 adjacent the second side edge 260. The bottom edge 256 includes a first strip light notch 266 adjacent the first side edge 258, a second strip light notch 268 adjacent the second side edge 260, and an elongated sky ceiling notch 270 between the first and second strip light notches 266, 268. Each of the joists 252 can be made from wood, engineered wood, or steel. In some embodiments, each of the joists 252 is made from wood having a thickness of 2 inches and a height of 8 inches.

Referring again to FIG. 3A, the front shell panel 232 of the lightbridge faceshell 230 is attached to the bottom edges 256 of the joists 252 with metal screw or like fasteners (not shown). The first side shell panel 234 of the lightbridge faceshell 230 is attached to the first side edges 258 of the joists 252 with metal screw or like fasteners (not shown), and the second side shell panel 236 of the lightbridge faceshell 230 is attached to the second side edges 260 of the joists 252 with metal screw or like fasteners (not shown).

Referring again to FIG. 3B, the first and second lightbridge ceiling attachment struts 272, 274 are respectively seated in the first and second attachment strut notches 262, 264 of each of the joists 252, and extend longitudinally from a distal-most joist 252d to a proximal-most joist 252p. Each of the attachment struts 272, 274 can be made from wood having a thickness of 2 inches and a height of 4 inches. The attachment struts 272, 274 are attached to the joists 252 with metal screw or like fasteners (not shown) that extend through the struts 272, 274 and into the bottoms of the attachment strut notches 262, 264.

Figure 3D:
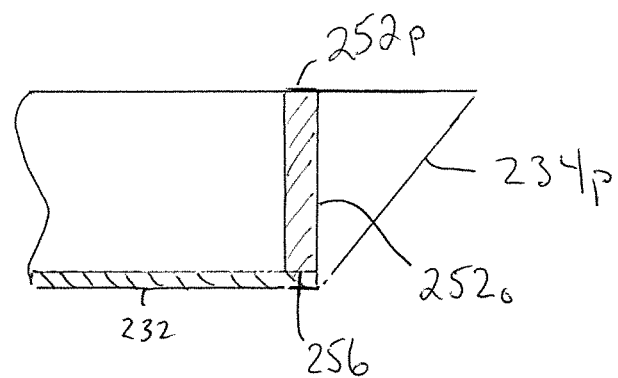
FIG. 3D is a cross-sectional side view of a proximal end of the lightbridge.

As shown in FIGS. 3A, 3B and 3D, the distal-most joist 252$d$ at the distal end 224 of the lightbridge 220 is positioned so that its outer-facing surface 252$o$ is flush with the distal edge of the front side shell panel 232$d$ and the perpendicular distal edges 234$d$, 236$d$ of the first and second side shell panels 234, 236 of the lightbridge faceshell 230. The proximal-most joist 252$p$ at the proximal end 222 of the lightbridge 220 is positioned so that its outer-facing surface 252$o$ at the bottom edge 256 thereof is flush with the proximal edge 232$p$ of the front side shell panel 232 and the bottoms of the proximal mitered edges 234$p$, 236$p$ (only proximal mitered edge 234$p$ of the second side shell panel 234 is shown in FIG. 3D) of the first and second side shell panels 234, 236 of the lightbridge faceshell 230. The tops of the proximal mitered edges 234$p$, 236$p$ (only the proximal mitered edge 234$p$ of the second side shell panel 234 is visible in FIG. 3D) of the first and second side shell panels 234, 236 of the lightbridge faceshell 230 extend past the proximal-most joist 252$p$. The proximal ends 272$p$, 274$p$ of the first and second attachment struts 272, 274 extend pass the proximal-most joist 252$p$.

Referring to FIG. 3B, the lightbridge 220 further includes two or more spaced apart lightbridge ceiling attaching assemblies 280. Each ceiling attaching assembly 280 is attached to one of the joists 252. In some embodiments, a first ceiling attaching assembly 280 is attached to the joist 252 located approximately in the center of the lightbridge support structure 250, and a second ceiling attaching assembly 280 is attached to the joist 252 approximately located between proximal-most joist 252$p$ and the joist with the first ceiling attaching assembly 280.

Figure 3F:
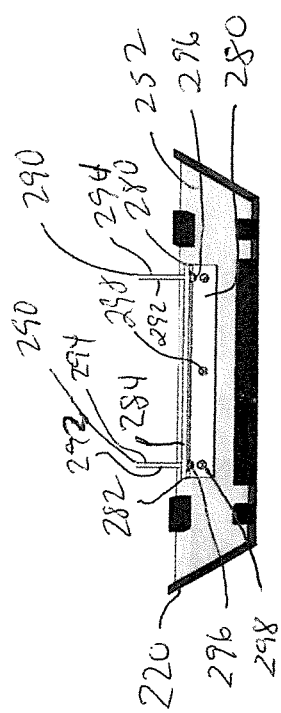
FIG. 3F is cross-sectional view of the lightbridge.

As shown in FIGS. 3E and 3F, each ceiling attaching assembly 280 includes an elongated L-shaped metal angle bracket 282 and two or more spaced apart threaded T-shaped connection rods 290. The metal angle bracket 282 includes a horizontally extending top leg 284 with a horizontally extending slot 286, and a vertically extending bottom leg 288. The elongated slot 286 of the top leg 284 receives the connection rods 290 and allows the rods 290 to be selectively located at any location along the slot 286. The bottom leg 288 allows the ceiling attaching assembly 280 to be attached to the joist 252 with two or more metal nut and bolt or like fastener arrangements 298. Each connection rod 290 has an elongated rod-like body 292 which is threaded 294 at one end and terminated at the other end with an enlarged head 296. Each connection rod 290 extends up through the slot 286 of the angle bracket top leg 284 with the threaded end 294 pointing up (toward the ceiling of the patient room) and the head 296 engaging the bottom of the top leg 284 so that the rod 290 does not pass through the slot 286. In some embodiments, when the modular insert is installed in the patient room, the threaded ends 294 of the connection rods 290 extend through a ceiling support structure (not shown) of the patient room ceiling so they can be terminated with a corresponding metal nut to allow the lightbridge 220 to be suspended from the ceiling support structure.

Referring now to FIG. 4, the lightbridge 220 can be assembled to the headwall 120 (absent the outer headwall faceshell 140) by positioning the lightbridge 220 at a right angle relative to the headwall 120. The proximal end 222 of the lightbridge is then aligned with the upper end 130 of the headwall 120 and the extended proximal ends 272$p$, 274$p$ of the first and second attachment struts 272, 274 are positioned on a top edge 198$t$ of the wall frame lightbridge support ledger 198 of the headwall 120. The extended proximal ends 272$p$, 274$p$ of the first and second attachment struts 272, 274 are then fastened to the wall frame lightbridge support ledger 198 with metal screw or like fasteners 276.

Figure 5B:
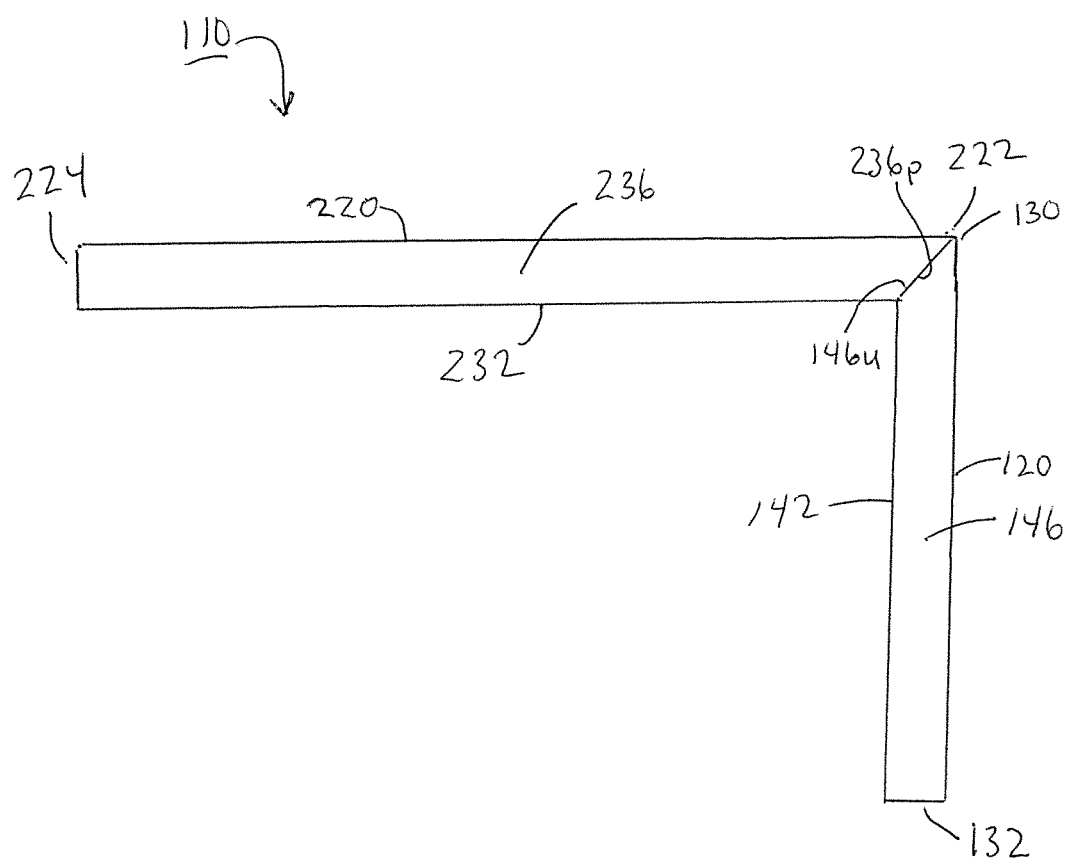
FIG. 5B is an elevational side view of the modular insert of FIG. 5A.

FIGS. 5A-5C show the completed modular insert 110 with lightbridge 220 attached to the headwall 120 and the outer headwall faceshell 140 attached to the inner wall panel arrangement and faceshell supports (not visible) of the headwall 120 (as would be case when the modular insert 110 is installed in the patient room as shown in FIG. 1). When attached, the mitered upper edges 144$u$, 146$u$ of the first and second side shell panels 144, 146 and the upper edge 142$u$ of the front shell panel 142 of the outer headwall faceshell 140 engage the mitered proximal edges 234$p$, 236$p$ of the first and second side shell panels 234, 236 and the proximal edge 232$p$ of the front shell panel 232 of the lightbridge faceshell 230 in a seamless manner.

Figure 6A:
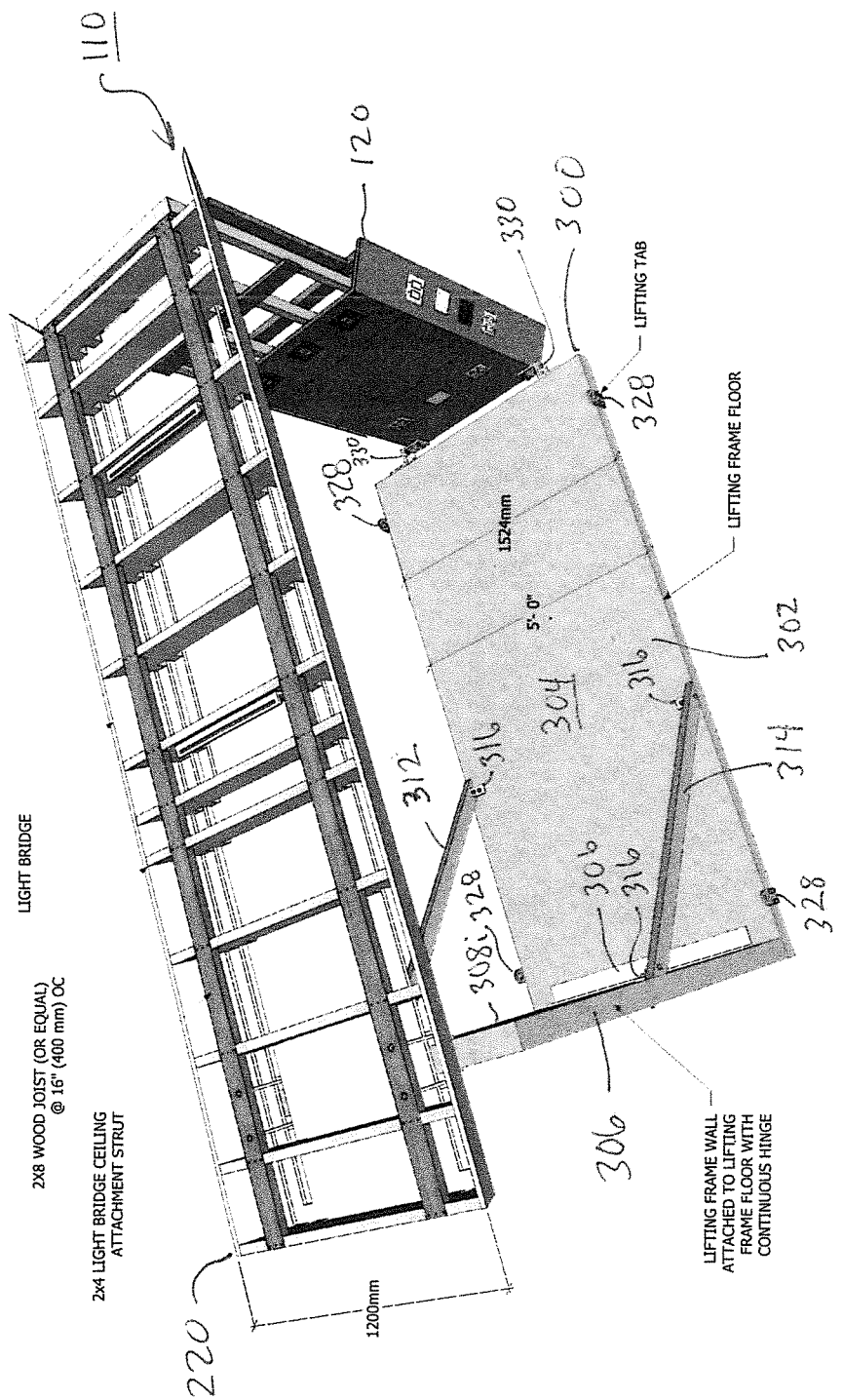
FIG. 6A is a perspective side view of the modular insert connected to an embodiment of a lifting frame.

Referring now to FIGS. 6A and 6B, there is shown a lifting frame 300, which removably attaches to the modular insert 110 after the lightbridge 220 has been attached to the headwall 120 during the manufacture of the modular insert 110 and prior to the installation of the headwall faceshell 140. The lifting frame 300 securely holds the lightbridge 220 and headwall 120 in position so that the modular insert 110 can be safely shipped to the medical care facility and easily installed in the patient room 100.

Referring still to FIGS. 6A and 6B, the lifting frame 300 includes a floor member 302 and a wall member 306, which members can be made of wood or metal. The wall member 306 is pivotally attached to the floor member 302 with one or more hinges or a continuous hinge 310, which has a first arm 310$a_1$ attached to an inner surface 308$i$ of the wall member 306 at a bottom end 306$b$ thereof with two or more metal screw or like fasteners (not shown) and a second arm 310$a_2$ attached to the marginal distal end 302$d$ of a floor surface 304 of the floor member 302 with two or more metal screw or like fasteners (not shown). First and second diagonal braces 312, 314 help hold the wall member 306 perpendicular to the floor member 302 under the load of the lightbridge 220. A first end of each diagonal brace 312, 314 is connected to the inner surface 308$i$ of the wall member 306 on each side thereof with an L-shaped metal angle bracket 316. Each angle bracket 316 has a first leg 316$_{L1}$ attached to the inner surface 308$i$ of the wall member 306 with a metal screw or like fastener 318, such as a metal nut and bolt arrangement and a second leg 316$_{L2}$ removably attached to the first end of the first diagonal brace 312, 314 with a metal nut and bolt or like fastener arrangement 320. A second end of each diagonal brace 312, 314 is connected to the floor surface 304 of the floor member 302 on each side edge thereof with a metal angle bracket 322. A first leg 322$_{L1}$ of the angle bracket 322 is attached to the floor surface 304 of the floor member 302 with a metal screw or like fastener 324, such as a metal nut and bolt arrangement, and a second leg (not visible) of the angle bracket 322 is removably attached to the second end of each diagonal brace 312, 314 with a metal nut and bolt or like fastener arrangement 326. Four metal lifting tabs 328 are attached to floor member 302. Each lifting tab 328 is attached to a side edge surface 302$_S$ of the floor member 302 near or at a corner of the floor member 302 with one or more a metal nut and bolt or like fastener arrangements 329 (FIG. 6C).

Referring now to FIG. 6C, the proximal end 302$p$ of the floor member 302 is removably attached to the headwall 120 with two metal angle bracket arrangements 330. Each metal angle bracket arrangement 330 can comprise a first metal angle bracket 332 having first and second legs $332_{L1}$, $332_{L2}$ and a second metal angle bracket 334 having first and second legs $334_{L1}$, $334_{L2}$. The first leg $332_{L1}$ of each first angle bracket 332 is removably attached to a proximal-end edge surface 302p of the floor member 302 with one or more a metal nut and bolt or like fastener arrangements 336 and the second leg $332_{L2}$ of each first angle bracket 322 is removably attached to the second leg $334_{L2}$ of each second angle bracket 334 with one or more a metal nut and bolt or like fastener arrangements 338. The first leg $334_{L1}$ of each second angle bracket 334 is removably attached to lower front panel 156 and the outer-most wall frame wall studs 180 of the headwall 120 with one or more a metal nut and bolt or like fastener arrangements 340.

Figure 6D:
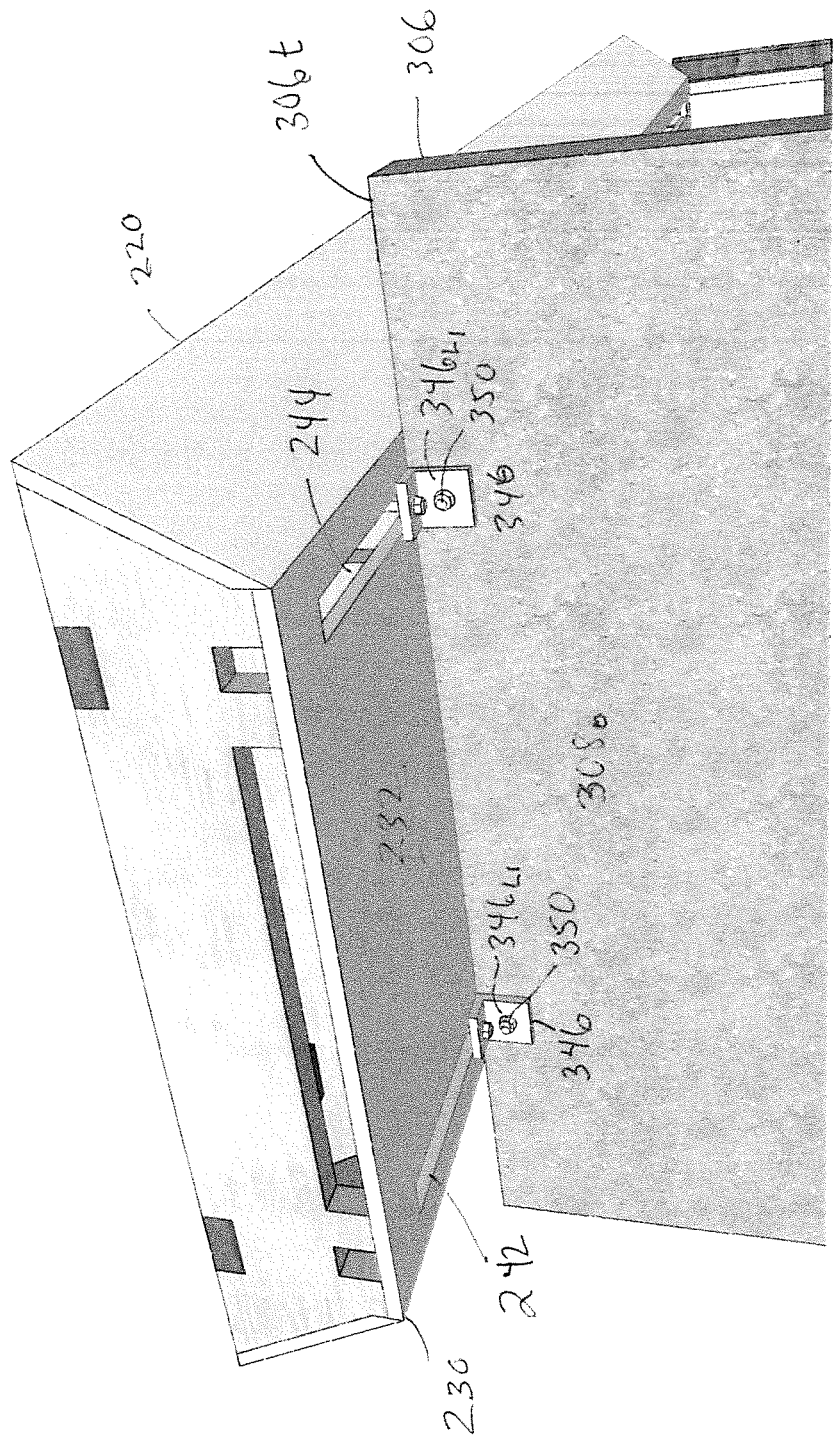
FIG. 6D is a perspective view showing a top end of a wall member of the lifting frame connected to a marginal distal end of the lightbridge of the modular insert.

As shown in FIG. 6D, a top end 306t of the lifting frame wall member 306 is removably attached to the lightbridge ceiling attachment struts 272, 274 with outer and inner pairs of metal nut and elongated bolt or like lifting frame fastener arrangements 342, 344 and outer and inner pairs of L-shaped metal angle brackets 346, 348. The outer pair of the angle brackets 346 are attached to the outer surface 308o of the wall member 306 at the top end 306t thereof, and the inner pair of the angle brackets 348 are attached to the inner surface 308i of the wall member 306 at the top end 306t thereof opposite the outer pair angle brackets 346 attached on the outer surface 308o. A metal nut and bolt or like fastener arrangement 350 is used to fasten first legs $346_{L1}$, $348_{L1}$ of each outer and inner pair of angle brackets 346, 348 to the wall member 306.

As shown in FIG. 6E, elongated bolts 342b, 344b of the outer and inner pairs of lifting frame fastener arrangements 342, 344 each extend through a corresponding one of the attachment struts 272, 274 and a corresponding one of the medical exam strip light openings 242, 244 in the front shell wall 232 of the lightbridge faceshell 230. The threaded ends of the elongated bolts 342b the outer pairs of lifting frame fastener arrangements 342 are removably fastened to second legs $346_{L2}$ of each outer pair of angle brackets 346 with nuts 342n of the outer pairs of the lifting frame fastener arrangements 342, and the threaded ends of the elongated bolts 344b the inner pairs of lifting frame fastener arrangements 344 are removably fastened to second legs $348_{L2}$ of each inner pair of angle brackets 348 with nuts 344n of the inner pairs of the lifting frame fastener arrangements 344.

Referring to FIGS. 7A and 7B, the modular insert 110 is installed in the patient room 100 by attaching the wall frame 170 of the headwall 120 to the first wall 102 of the patient room 100. The lightbridge 220 of the modular insert 110 is attached to ceiling (not visible) with the connection rods 290 of the lightbridge ceiling attaching assemblies 280, which can be attached to the ceiling support structure (not shown) of the patient room ceiling. The distal-most joist 252d of the lightbridge support structure 250 is then attached to the wall 108 of the patient room 100 with metal screw or like fasteners 253. Once installed, the lifting frame 300 can be removed from the headwall 120 and the lightbridge 220 by unfastening the metal nut and bolt or like fastener arrangements 340 which attach the floor wall 302 of the lifting frame 300 to the lower front panel 156 and the frame wall studs 180 of the headwall 120 and unfastening the outer and inner pairs of lifting frame fastener arrangements 342, 344 which attach the attachment struts 272, 274 of the lightbridge support structure 250 to the wall member 306 of the lifting frame 300.

It should be understood that the invention is not limited to the embodiments illustrated and described herein. Rather, the appended claims should be construed broadly to include other variants and embodiments of the invention, which may be made by those skilled in the art without departing from the scope and range of equivalents of the invention. It is indeed intended that the scope of the invention should be determined by proper interpretation and construction of the appended claims and their legal equivalents, as understood by those of skill in the art relying upon the disclosure in this specification and the attached drawings.

What is claimed is:

1. A modular insert for a patient room, the modular insert comprising:
    a headwall with supply connections for electricity and medical grade vacuum, air and oxygen; and
    a lightbridge with medical examination lighting, the lightbridge having an isosceles trapezoidal cross-sectional shape and coupled to the headwall;
    wherein the lightbridge comprises a faceshell having a rectangular, planar front shell panel having first and second side edges and a rectangular planar side shell panel depending from each of the first and second side edges of the front shell panel, wherein the front shell panel and the side shell panels of the faceshell are attached to an internal support structure and enclose bottom and side portions of the internal support structure, and wherein the planar front shell panel includes an elongated opening;
    wherein the medical examination lighting comprises a medical examination light strip disposed in the elongated opening of the planar front shell panel of the faceshell;
    wherein the headwall comprises an inner panel arrangement; and
    wherein the supply connections are provided by the inner panel arrangement.

2. A modular insert for a patient room, the modular insert comprising:
    a headwall with supply connections for electricity and medical grade vacuum, air and oxygen; and
    a lightbridge with medical examination lighting, the lightbridge having an isosceles trapezoidal cross-sectional shape and coupled to the headwall;
    wherein the lightbridge comprises a faceshell and an internal support structure for supporting the faceshell, wherein the faceshell and the support structure are separate from the headwall;
    wherein the faceshell of the lightbridge comprises a rectangular, planar front shell panel having first and second side edges and a rectangular planar side shell panel depending from each of the first and second side edges of the front shell panel, and wherein the front shell panel and the side shell panels of the faceshell are attached to the internal support structure and enclose bottom and side portions of the internal support structure; and
    wherein the support structure includes a plurality of spaced apart joists that extend transversely between the side shell panels and at least one ceiling attachment strut attached to the joists.

3. The modular insert according to claim 2, wherein one end of the lightbridge is coupled to a top end of the headwall, thereby forming an L-shaped configuration, such that when the modular insert is installed in the patient room, the headwall extends along a side wall of the patient room and the lightbridge extends along a ceiling of the patient room.

4. The modular insert according to claim 2, wherein the headwall comprises an inner panel arrangement, wherein the supply connections are provided by the inner panel arrangement.

5. The modular insert according to claim 4, wherein the headwall further comprises a removable faceshell disposed over the inner panel arrangement, the faceshell including at least one window for accessing the supply connections.

6. The modular insert according to claim 5, further comprising a wall frame, wherein the inner panel arrangement and the faceshell of the headwall are attached to the wall frame.

7. The modular insert according to claim 4, wherein the inner panel arrangement comprises a removable access panel.

8. The modular insert according to claim 4, wherein the inner panel arrangement of the headwall comprises a front wall.

9. The modular insert according to claim 8, wherein the supply connections are provided by the front wall.

10. The modular insert according to claim 4, wherein the inner panel arrangement of the headwall comprises at least one side wall.

11. The modular insert according to claim 10, wherein the supply connections are further provided on the at least one side wall.

12. The modular insert according to claim 2, wherein the headwall is adapted to be electrically connected to electrical power of the patient room and supplies the lightbridge with electricity for the medical examination lighting.

13. The modular insert according to claim 12, wherein the headwall comprises a control device for the medical examination lighting of the lightbridge.

14. The modular insert according to claim 2, wherein the support structure further includes at least one ceiling attaching assembly.

15. The modular insert according to claim 2, wherein the faceshell of the lightbridge includes the medical examination lighting.

16. The modular insert according to claim 2, wherein the faceshell of the lightbridge of the lightbridge includes an illuminable sky ceiling panel.

17. The modular insert according to claim 2, further comprising a lifting frame removably attached to the modular insert, the lifting frame for transporting the modular insert to a patient room and facilitating installation of the modular insert in the patient room.

18. The modular insert according to claim 17, wherein the lifting frame comprises a floor member removably attached to the headwall and a wall member removably attached to the lightbridge.

19. The modular insert according to claim 18, wherein the wall member is pivotally attached to the floor member.

20. The modular insert according to claim 18, further comprising at least one brace extending between the floor and wall members, the at least one brace holding the wall member in a fixed position relative to the floor member.

21. A patient room comprising the modular insert of claim 2, wherein the patient room includes a wall and a ceiling, and wherein the modular insert is attached to at least one of the wall and the ceiling of the patient room.

* * * * *